United States Patent
Hon et al.

(10) Patent No.: US 11,031,101 B2
(45) Date of Patent: Jun. 8, 2021

(54) FINDING RELATIVES IN A DATABASE

(71) Applicant: 23andMe, Inc., Sunnyvale, CA (US)

(72) Inventors: Lawrence Hon, Sunnyvale, CA (US); Serge Saxonov, Oakland, CA (US); Brian Thomas Naughton, Mountain View, CA (US); Joanna Louise Mountain, Menlo Park, CA (US); Anne Wojcicki, Palo Alto, CA (US); Linda Avey, Lafayette, CA (US)

(73) Assignee: 23andMe, Inc., Sunnyvale, CA (US)

( * ) Notice: Subject to any disclaimer, the term of this patent is extended or adjusted under 35 U.S.C. 154(b) by 0 days.

(21) Appl. No.: 17/073,095

(22) Filed: Oct. 16, 2020

(65) Prior Publication Data

US 2021/0074385 A1  Mar. 11, 2021

Related U.S. Application Data

(63) Continuation of application No. 16/129,645, filed on Sep. 12, 2018, which is a continuation of application
(Continued)

(51) Int. Cl.
*G06F 16/9535* (2019.01)
*G16B 50/00* (2019.01)
(Continued)

(52) U.S. Cl.
CPC .......... *G16B 50/00* (2019.02); *G06F 16/2457* (2019.01); *G06F 16/9535* (2019.01);
(Continued)

(58) Field of Classification Search
CPC .................... G06F 16/2457; G06F 16/9535
See application file for complete search history.

(56) References Cited

U.S. PATENT DOCUMENTS 5,376,526 A   12/1994 Brown et al.
6,750,011 B1   6/2004 Perlin
(Continued)

FOREIGN PATENT DOCUMENTS

EP        0 967 291 A1    12/1999
WO   WO 2004/029298 A2    4/2004
(Continued)

OTHER PUBLICATIONS

Sun-Wei Guo, "Proportion of Genome Shared Identical by Descent by Relatives: Concept, Computation and Applications", 1995, American Society of Human Genetics, 56, 1468-1476. (Year: 1995).*
(Continued)

*Primary Examiner* — Sheryl L Holland
(74) *Attorney, Agent, or Firm* — Weaver Austin Villeneuve & Sampson LLP; David K. Buckingham

(57) ABSTRACT

Determining relative relationships of people who share a common ancestor within at least a threshold number of generations includes: receiving recombinable deoxyribonucleic acid (DNA) sequence information of a first user and recombinable DNA sequence information of a plurality of users; processing, using one or more computer processors, the recombinable DNA sequence information of the plurality of users in parallel; determining, based at least in part on a result of processing the recombinable DNA information of the plurality of users in parallel, a predicted degree of relationship between the first user and a user among the plurality of users, the predicted degree of relative relationship corresponding to a number of generations within which the first user and the second user share a common ancestor.

30 Claims, 15 Drawing Sheets

Related U.S. Application Data

No. 15/264,493, filed on Sep. 13, 2016, now abandoned, which is a continuation of application No. 13/871,744, filed on Apr. 26, 2013, now abandoned, which is a continuation of application No. 12/644,791, filed on Dec. 22, 2009, now Pat. No. 8,463,554.

(60) Provisional application No. 61/204,195, filed on Dec. 31, 2008.

(51) Int. Cl.
*G06F 16/2457* (2019.01)
*G06N 5/04* (2006.01)
*G16B 10/00* (2019.01)
*G16B 30/00* (2019.01)

(52) U.S. Cl.
CPC ............ *G06N 5/048* (2013.01); *G16B 10/00* (2019.02); *G16B 30/00* (2019.02)

(56) References Cited

U.S. PATENT DOCUMENTS

| | | | |
|---|---|---|---|
| 6,812,339 | B1 | 11/2004 | Venter et al. |
| 6,887,666 | B1 | 5/2005 | Hager |
| 7,107,155 | B2 | 9/2006 | Frudakis |
| 7,818,281 | B2 | 10/2010 | Kennedy et al. |
| 7,957,907 | B2 | 6/2011 | Sorenson et al. |
| 8,187,811 | B2 | 5/2012 | Eriksson et al. |
| 8,428,886 | B2 | 4/2013 | Wong et al. |
| 8,463,554 | B2 * | 6/2013 | Hon ............... G16B 10/00 702/19 |
| 8,510,057 | B1 | 8/2013 | Avey et al. |
| 8,543,339 | B2 | 9/2013 | Wojcicki et al. |
| 8,589,437 | B1 | 11/2013 | Khomenko et al. |
| 8,645,343 | B2 | 2/2014 | Wong et al. |
| 8,738,297 | B2 | 5/2014 | Sorenson et al. |
| 8,786,603 | B2 | 7/2014 | Rasmussen et al. |
| 8,855,935 | B2 | 10/2014 | Myres et al. |
| 8,990,250 | B1 | 3/2015 | Chowdry et al. |
| 9,116,882 | B1 | 8/2015 | Macpherson et al. |
| 9,213,944 | B1 | 12/2015 | Do et al. |
| 9,213,947 | B1 | 12/2015 | Do et al. |
| 9,218,451 | B2 | 12/2015 | Wong et al. |
| 9,336,177 | B2 | 5/2016 | Hawthorne et al. |
| 9,367,800 | B1 | 6/2016 | Do et al. |
| 9,390,225 | B2 | 7/2016 | Barber et al. |
| 9,405,818 | B2 | 8/2016 | Chowdry et al. |
| 9,836,576 | B1 | 12/2017 | Do et al. |
| 9,864,835 | B2 * | 1/2018 | Avey ............... G16B 45/00 |
| 10,025,877 | B2 | 7/2018 | Macpherson |
| 10,162,880 | B1 | 12/2018 | Chowdry et al. |
| 10,275,569 | B2 | 4/2019 | Avey et al. |
| 10,296,847 | B1 | 5/2019 | Do et al. |
| 10,432,640 | B1 | 10/2019 | Hawthorne et al. |
| 10,516,670 | B2 | 12/2019 | Hawthorne et al. |
| 10,572,831 | B1 | 2/2020 | Do et al. |
| 10,643,740 | B2 | 5/2020 | Avey et al. |
| 10,658,071 | B2 | 5/2020 | Do et al. |
| 10,691,725 | B2 | 6/2020 | Naughton et al. |
| 10,699,803 | B1 | 6/2020 | Do et al. |
| 10,755,805 | B1 | 8/2020 | Do et al. |
| 10,777,302 | B2 | 9/2020 | Chowdry et al. |
| 10,790,041 | B2 | 9/2020 | Macpherson et al. |
| 10,841,312 | B2 | 11/2020 | Hawthorne et al. |
| 10,854,318 | B2 | 12/2020 | Macpherson et al. |
| 10,891,317 | B1 | 1/2021 | Chowdry et al. |
| 2003/0101000 | A1 | 5/2003 | Bader et al. |
| 2003/0113727 | A1 | 6/2003 | Girn et al. |
| 2003/0165926 | A1 | 9/2003 | Olek et al. |
| 2003/0172065 | A1 | 9/2003 | Sorenson et al. |
| 2003/0203370 | A1 | 10/2003 | Yakhini et al. |
| 2003/0204418 | A1 | 10/2003 | Ledley |
| 2004/0122705 | A1 | 6/2004 | Sabol et al. |
| 2004/0126840 | A1 | 7/2004 | Cheng et al. |
| 2004/0229231 | A1 | 11/2004 | Frudakis et al. |
| 2004/0248086 | A9 | 12/2004 | Ginns et al. |
| 2005/0064476 | A1 | 3/2005 | Huang et al. |
| 2005/0089852 | A1 | 4/2005 | Lee et al. |
| 2005/0147947 | A1 | 7/2005 | Cookson, Jr. et al. |
| 2005/0191731 | A1 | 9/2005 | Judson et al. |
| 2005/0228595 | A1 | 10/2005 | Cooke et al. |
| 2006/0020398 | A1 | 1/2006 | Vernon et al. |
| 2006/0025929 | A1 | 2/2006 | Eglington |
| 2006/0136143 | A1 | 6/2006 | Avinash et al. |
| 2006/0257888 | A1 | 11/2006 | Zabeau et al. |
| 2007/0037182 | A1 | 2/2007 | Gaskin et al. |
| 2007/0111247 | A1 | 5/2007 | Stephens et al. |
| 2007/0250809 | A1 | 10/2007 | Kennedy et al. |
| 2008/0040046 | A1 | 2/2008 | Chakraborty et al. |
| 2008/0081331 | A1 * | 4/2008 | Myres .............. G16B 45/00 435/6.11 |
| 2008/0131887 | A1 | 6/2008 | Stephan et al. |
| 2008/0154566 | A1 | 6/2008 | Myres et al. |
| 2008/0189047 | A1 | 8/2008 | Wong et al. |
| 2009/0099789 | A1 | 4/2009 | Stephan et al. |
| 2009/0118131 | A1 | 5/2009 | Avey et al. |
| 2009/0119083 | A1 | 5/2009 | Avey et al. |
| 2009/0319610 | A1 * | 12/2009 | Nikolayev ......... G06Q 10/10 709/204 |
| 2009/0326832 | A1 | 12/2009 | Heckerman et al. |
| 2010/0042438 | A1 | 2/2010 | Moore et al. |
| 2010/0070455 | A1 | 3/2010 | Halperin et al. |
| 2010/0223281 | A1 | 9/2010 | Hon et al. |
| 2012/0270794 | A1 | 10/2012 | Eriksson et al. |
| 2013/0345988 | A1 | 12/2013 | Avey et al. |
| 2014/0006433 | A1 | 1/2014 | Hon et al. |
| 2014/0067355 | A1 | 3/2014 | Noto et al. |
| 2015/0100243 | A1 | 4/2015 | Myres et al. |
| 2015/0227610 | A1 | 8/2015 | Chowdry et al. |
| 2016/0026755 | A1 | 1/2016 | Byrnes et al. |
| 2016/0103950 | A1 | 4/2016 | Myres et al. |
| 2016/0171155 | A1 | 6/2016 | Do et al. |
| 2016/0277408 | A1 | 9/2016 | Hawthorne et al. |
| 2016/0350479 | A1 | 12/2016 | Han et al. |
| 2017/0011042 | A1 | 1/2017 | Kermany et al. |
| 2017/0017752 | A1 | 1/2017 | Noto et al. |
| 2017/0220738 | A1 | 8/2017 | Barber et al. |
| 2017/0228498 | A1 | 8/2017 | Hon et al. |
| 2017/0277827 | A1 | 9/2017 | Granka et al. |
| 2017/0277828 | A1 | 9/2017 | Avey et al. |
| 2017/0329866 | A1 | 11/2017 | Macpherson |
| 2017/0329891 | A1 | 11/2017 | Macpherson et al. |
| 2017/0329899 | A1 | 11/2017 | Bryc et al. |
| 2017/0329901 | A1 | 11/2017 | Chowdry et al. |
| 2017/0329902 | A1 | 11/2017 | Bryc et al. |
| 2017/0329904 | A1 | 11/2017 | Naughton et al. |
| 2017/0329915 | A1 | 11/2017 | Kittredge et al. |
| 2017/0329924 | A1 | 11/2017 | Macpherson et al. |
| 2017/0330358 | A1 | 11/2017 | Macpherson et al. |
| 2018/0181710 | A1 | 6/2018 | Avey et al. |
| 2018/0307778 | A1 | 10/2018 | Macpherson |
| 2019/0012431 | A1 | 1/2019 | Hon et al. |
| 2019/0114219 | A1 | 4/2019 | Do et al. |
| 2019/0139623 | A1 | 5/2019 | Bryc et al. |
| 2019/0206514 | A1 | 7/2019 | Avey et al. |
| 2019/0267115 | A1 | 8/2019 | Avey et al. |
| 2020/0137063 | A1 | 4/2020 | Hawthorne et al. |
| 2020/0372974 | A1 | 11/2020 | Chowdry et al. |
| 2021/0043278 | A1 | 2/2021 | Hon et al. |
| 2021/0043279 | A1 | 2/2021 | Hon et al. |
| 2021/0043280 | A1 | 2/2021 | Hon et al. |
| 2021/0043281 | A1 | 2/2021 | Macpherson et al. |

FOREIGN PATENT DOCUMENTS

| | | |
|---|---|---|
| WO | WO 2006/089238 A3 | 8/2006 |
| WO | WO 2007/084902 | 7/2007 |
| WO | WO 2008/042232 A2 | 4/2008 |
| WO | WO 2016/073953 | 5/2016 |

(56) References Cited

OTHER PUBLICATIONS

Office Action dated May 31, 2012 in U.S. Appl. No. 12/644,791.
Final Office Action dated Dec. 7, 2012 in U.S. Appl. No. 12/644,791.
Notice of Allowance dated Feb. 25, 2013 in U.S. Appl. No. 12/644,791.
Office Action dated Feb. 18, 2016 in U.S. Appl. No. 13/871,744.
Office Action dated Mar. 14, 2016 in U.S. Appl. No. 13/871,744.
Office Action dated May 18, 2018 in U.S. Appl. No. 15/264,493.
Office Action dated Mar. 3, 2020 in U.S. Appl. No. 15/664,619.
Notice of Allowance dated Aug. 19, 2020 in U.S. Appl. No. 15/664,619.
International Search Report and Written Opinion dated Mar. 3, 2010 in PCT/US2009/06706.
International Preliminary Report on Patentability dated Jul. 5, 2011 in PCT/US2009/06706.
International Preliminary Report on Patentability dated Apr. 7, 2009 in PCT Application No. PCT/US2007/020884.
Written Opinion dated Apr. 8, 2008 in PCT Application No. PCT/US2007/020884.
International Search Report dated Apr. 8, 2008 in PCT Application No. PCT/US2007/020884.
Extended European Search Report dated Oct. 25, 2016 in EP 09836517.4.
International Preliminary Report on Patentability dated Jul. 14, 2011 in PCT/US2009/006706.
Extended European Search Report dated Oct. 9, 2017 in Application No. 17172048.5.
Abecasis, et al., "Extent and distribution of linkage disequilibrium in three genomic regions" Am. J. Hum. Genet. 68, (2001) pp. 191-197.
Abecasis, et al., "GOLD—Graphical overview of linkage disequilibrium" Bioinformatics, vol. 16, No. 2, (2000) pp. 182-183.
Abecasis, et al., "GRR: graphical representation of relationship errors" Bioinformatics 17, (2001) pp. 742-743.
Abecasis, et al., "Handling marker-marker linkage disequilibrium: pedigree analysis with clustered markers" Am. J. Hum. Genet. 77 (2005) pp. 754-767.
Abecasis, et al., "Linkage disequilibrium: ancient history drives the new genetics" Hum. Hered. 59, (2005) pp. 118-124.
Abecasis, et al., "MaCH: Using sequence and genotype data to estimate haplotypes and unobserved genotypes" Genetic Epidemiology 34 (2010) pp. 816-834.
Abecasis, et al., "Merlin-rapid analysis of dense genetic maps using sparse gene flow trees" Nat. Genet. 2002, 30 (2002) pp. 97-101.
Abney, et al., "Quantitative-Trait Homozygosity and Association Mapping and Empirical Genomewide Significance in Large, Complex Pedigrees: Fasting Serum-Insulin Level in the Hutterites" Am. J. Hum. Genet. 70, (2002) pp. 920-934.
Albers, et al., "Multipoint Approximations of Identity-by-descent probabilities for accurate linkage analysis of distantly related individuals," The American Journal of Human Genetics 82, Mar. 2008, pp. 607-622.
Alexander, et al., "Fast model-based estimation of ancestry in unrelated individuals" Genome Research 19, (2009) pp. 1655-1664.
Almasy, et al. "Multipoint quantitative-trait linkage analysis in general pedigrees" Am. J. Hum. Genet. 62: (1998) pp. 1198-1211.
Almudevar, A., "A Bootstrap Assessment of Variability in Pedigree Reconstruction Based on DNA Markers" Biometrics, vol. 57, Sep. 2001, pp. 757-763.
Almudevar, A., "A simulated annealing algorithm for maximum likelihood pedigree reconstruction" Theoretical Population Biology, vol. 63, (2003) pp. 63-75.
Almudevar, et al., "Estimation of single-generation sibling relationship based on DNA markers" Journal Agricultural Biological, and Environmental Statistics, vol. 4, No. 2, (1999) pp. 136-165.
Almudevar, et al., "Most powerful permutation invariant tests for relatedness hypotheses based on genotypic data" Biometrics 57, Dec. 2001, pp. 1080-1088.
Altschul, et al. "Basic Local Alignment Search Tool" J. Mol. Biol. (1990) 215, pp. 403-410.
Amorim, et al., "Pros and cons in the use of SNP's in forensic kinship investigation: a comparative analysis with STRs" Forensic Sci. Int. 150, (2005) pp. 17-21.
Amos and Elston, "Robust Methods for the Detection of Genetic Linkage for Quantitative Data From Pedigree" Genetic Epidemiology 6, (1989) pp. 349-360.
Amos, et al., "The Probabilistic Determination of Identity-by-Descent Sharing for Pairs of Relatives from Pedigrees" Am. J. Hum. Genet. 47 (1990) pp. 842-853.
Ayers, et al. "Reconstructing Ancestral Haplotypes with a Dictionary Model" Department of Statistics Papers, Department of Statistics, UCLA, UC Los Angeles, Mar. 28, 2005, pp. 1-41.
Bacolod, et al., "The Signatures of Autozygosity among Patients with Colorectal Cancer" Cancer Res. vol. 68, No. 8, Apr. 15, 2008, pp. 2610-2621.
Balding, et al., "A method for quantifying differentiation between populations at multi-allelic loci and its implications for investigating identity and paternity" Genetica, 96 (1995) pp. 3-12.
Ballantyne, J., "Mass disaster genetics" Nature Genet. 15, (1997) pp. 329-331.
Belkhir, et al., "IDENTIX, a software to test for relatedness in a population using permutation methods" Molecular Ecology, 2, (2002) pp. 611-614.
Bieber, et al., "Finding criminals through DNA of their relatives" Science 312, (2006) pp. 1315-1316.
Blackwell et al., "Identity by Descent Genome Segmentation Based on Single Nucleotide Polymorphism Distributions," American Association for Artificial Intelligence, 1999, pp. 54-59.
Blouin, M.S. et al., "Use of microsatellite loci to classify individuals by relatedness" Molecular Ecology, vol. 5, (1996) pp. 393-401.
Blouin, M.S., "DNA-based methods for pedigree reconstruction and kinship analysis in natural populations" Trends in Ecology and Evolution, vol. 18, No. 10, Oct. 2003, pp. 503-511.
Boehnke, et al., "Accurate Inference of Relationships in Sib-Pair Linkage Studies" Am. J. Hum. Genet. 61, (1997) pp. 423-429.
Boehnke, M., "Allele frequency estimation from data on relatives" Am. J. Hum. Genet. 48, (1991) pp. 22-25.
Brenner, C.H. "Kinship Analysis by DNA When There Are Many Possibilities" Progress in Forensic Genetics, vol. 8, (2000) pp. 94-96, Elsevier Science.
Brenner, C.H., "Issues and strategies in the DNA identification of World Trade Center victims" Theor. Popul. Biol. 63, (2003) pp. 173-178.
Brenner, C.H., "Symbolic kinship program" Genetics, 145, (1997) pp. 535-542.
Brief for Defendants—Appellees Ancestry.com DNA, LLC, Ancestry.com Operations Inc., and Ancestry.com LLC, Case No. 2019-1222, Document: 24, Filed on Mar. 18, 2019, in the US Court of Appeals for the Federal Circuit, pp. 1-76.
Brief of Appellant 23AndMe, Inc., Case No: 2019-1222, Document 19, Filed on Feb. 4, 2019, in the US Court of Appeals for the Federal Circuit, pp. 1-140.
Broman, et al., "Estimation of pairwise relationships in the presence of genotyping errors" Am. J. Hum. Genet. 63, (1998) pp. 1563-1564.
Broman, et al., "Long Homozygous Chromosomal Segments in Reference Families from the Centre d'E'tude du Polymorphisme Humain" Am. J. Hum. Genet. 65, (1999) pp. 1493-1500.
Browning, et al., "A unified approach to Genotype imputation and Haplotype-Phase inference for large data sets of Trios and unrelated individuals" Am. J. Hum. Genet. 84, (2009) pp. 210-223.
Browning, et al., "Efficient Multilocus Association Testing for Whole Genome Association Studies Using Localized Haplotype Clustering" Genetic Epidemiology, vol. 31, 2007 pp. 365-375.
Browning, et al., "On reducing the statespace of hidden markov models for the identity by descent process" Theor. Popul. Biol. 62, (2002) pp. 1-8.
Browning, et al., "Rapid and Accurate Haplotype Phasing and Missing-Data Inference for Whole-Genome Association Studies by Use of Localized Haplotype Clustering," The American Journal of Human Genetics, vol. 81, Nov. 2007, pp. 1084-1097.

(56) References Cited

OTHER PUBLICATIONS

Browning, et al., "Identity by Descent Between Distant Relatives: Detection and Applications." Annual Review of Genetics, vol. 46, Dec. 2012, pp. 617-633.
Browning, S. et al., "Estimation of pairwise identity by descent from dense genetic marker data in a population sample of haplotypes," Genetics, vol. 178, No. 4, Apr. 22, 2008, pp. 2123-2132. <doi: 10.1534/genetics.107.084624>.
Cannings, C., "The identity by descent process along the chromosome" Human Heredity, 56 (2003) pp. 126-130.
Carlson, et al., "Mapping complex disease loci in whole-genome association studies" Nature 429 (2004) pp. 446-452.
Cavalli-Sforza, L., "The Human Genome Diversity Project: past, present and future," Nature Reviews, Genetics, vol. 6, Apr. 2005, pp. 333-340.
Chapman, et al., "The effect of population history on the lengths of ancestral chromosome segments" Genetics, 162, Sep. 2002, pp. 449-458.
Chen et al., "Family-Based Association Test for Genomewide Association Scans," The American Journal of Human Genetics, vol. 81, Nov. 2007, pp. 913-926.
Chen, et al., "Robust relationship inference in genome-wide association studies" Bioinformatics 26 No. 22, 2010, pp. 2867-2873.
Cheung, et al., "Linkage-disequilibrium mapping without genotyping" Nature Genetics 18, (1998) pp. 225-230.
Choi, et al., "Case-control association testing in the presence of unknown relationships" Genet. Epidem. 33, (2009) pp. 668-678.
Cockerman, C., "Higher order probability functions of identity of alleles by descent" Genetics 69, (1971) pp. 235-246.
Complaint filed in the United States District Court in and for the Northern District of California, captioned *23andMe, Inc.* v. *Ancestry. com DNA, LLC, Ancestry.com Operations Inc., and Ancestry.com LLC*, filed on May 11, 2018, assigned Case No. 18-cv-02791-JCS, for "Complaint for Patent Infringement, Violations of the Lanham Act, Cal. Bus. & Prof. Code §§ 17200 and 17500, and Declaratory Relief of No Trademark Infringement and Trademark Invalidity."
Cordell, et al., "Two-locus maximum Lod score analysis of a multifactorial trait: joint consideration of IDDM2 and IDDM4 with IDDM1 in Type 1 diabetes" Am. J. Hum. Genet. 57, (1995) pp. 920-934.
Cowell, R.G., "FINEX: A probabilistic expert system for forensic identification" Forensic Science International, 134, (2003) pp. 196-206.
Crawford, et al., "Evidence for substantial fine-scale variation in recombination rates across the human genome," Nature Genetics, vol. 36, No. 7, Jul. 2004, pp. 700-706.
Cudworth, et al., "Evidence for HL-A-linked genes in "juvenile" diabetes mellitus" Br. Med. J. 3, (1975) pp. 133-135.
Curtis, et al., "Using risk calculation to implement an extended relative pair analysis" Ann. Hum. Genet. 58 (1994) pp. 151-162.
Defendants' Notice of Motion and Motion to Dismiss Plaintiff's Complaint, filed in the United States District Court in and for the Northern District of California LLC on Jun. 29, 2018, Case No. 18-cv-02791-JCS, Re *23andMe, Inc.* v. *Ancestry.com DNA, LLC, Ancestry.com Operations Inc., and Ancestry.com*.
Delaneau, et al., "A Linear complexity phasing method for thousands of genomes," Nature Methods, vol. 9, No. 2, Feb. 2012, pp. 179-184.
Denniston, C., "Probability and genetic relationship" Ann. Hum. Genet., Lond. (1975), 39, pp. 89-103.
Di Rienzo, et al., "An evolutionary framework for common diseases: the ancestral-susceptibility model" Trends Genet. 21 (2005) pp. 596-601.
Dodds, et al. "Using genetic markers in unpedigreed populations to detect a heritable trait" J. Zhejiang Univ. Sci. 2007 8(11):782-786.
Donnelly, K.P., "The probability that related individuals share some section of genome identical by descent" Theor. Popul. Biol. 23 (1983) pp. 34-63.

Douglas, et al., "A multipoint method for detecting genotyping errors and mutations in sibling-pair linkage data" Am. J. Hum. Genet. 66 (2000) pp. 1287-1297.
Duffy, et al. "An integrated genetic map for linkage analysis" Behav. Genet. 36, 2006, pp. 4-6.
Dupuis, et al., "Statistical methods for linkage analysis of complex traits from high resolution maps of identity by descent" Genetics 140 (1995) pp. 843-856.
Eding, et al., "Marker-based estimates of between and within population kinships for the conservation of genetic diversity" J. Anim. Breed. Genet. 118 (2001), pp. 141-159.
Ehm, et al., "A test statistic to detect errors in sib-pair relationships" Am. J. Hum. Genet. 62 (1998) pp. 181-188.
Elston, et al., "A general model for the genetic analysis of pedigree data" Hum. Hered. 21, (1971) pp. 523-542.
Epstein, et al., "Improved inference of relationship for pairs of individuals" Am. J. Hum. Genet., vol. 67, (2000) pp. 1219-1231.
Falush, et al., "Inference of population structure using multilocus genotype data:linked loci and correlated allele frequencies" Genetics 164, (2003) pp. 1567-1587.
Feingold, E. "Markov processes for modeling and analyzing a new genetic mapping method" J. Appl. Prob. 30 (1993) pp. 766-779.
Feingold, et al., "Gaussian Models for Genetic Linkage Analysis Using Complete High-Resolution Maps of Identity by Descent," Am. J. Hum. Genet. 53 (1993) pp. 234-251.
Fisher, RA "A Fuller Theory of 'Junctions' in Inbreeding" Heredity, 8 (1954) pp. 187-197.
Fisher, RA "The theory of inbreeding" Department of Genetics, Cambridge University, Eng. Edinburgh, London, Oliver & Boyd, Ltd., (1949) pp. 97-100.
Frazer, et al., "A second generation human haplotype map of over 3.1 million SNPs" vol. 449, Oct. 18, 2007, pp. 851-861. <doi:10. 1038/nature06258>.
Fuchsberger, et al., "Minimac2: faster genotype imputation," Bioinformatics, vol. 31, No. 5, Oct. 22, 2014, pp. 782-784. <doi:10. 1093/bioinformatics/btu704>.
Gaytmenn, et al., "Determination of the sensitivity and specificity of sibhip calculations using AmpF/STR Profiler Plus" Int. J. Legal Med. 116, (2002) pp. 161-164.
George, et al., "Discovering disease genes: Multipoint linkage analyses via a new Markov Chain Monte Carlo approach" Statistical Science, vol. 18, No. 4, (2003) pp. 515-535.
Gillanders, et al., "The Value of Molecular Haplotypes in a Family-Based Linkage Study" Am. J. Hum. Genet. 79 (2006) pp. 458-468.
Glaubitz, et al., "Prospects for inferring pairwise relationships with single nucleotide polymorphisms" Molecular Ecology, 12 (2003) pp. 1039-1047.
Goodnight, et al., "Computer software for performing likelihood tests of pedigree relationship using genetic markers" Molecular Ecology, vol. 8, (1999) pp. 1231-1234.
Grafen, A., "A geometric view of relatedness" Oxford Surveys in Evolutionary Biology, 2 (1985) pp. 39-89.
Grant, et al., "Significance testing for direct identity-by-descent mapping" Ann. Hum. Genet. 63, (1999) pp. 441-454.
Greenspan, et al., "Model-based inference of haplotype block variation" J. Comput. Biol. 11, (2004) pp. 493-504.
Griffiths, et al., "Ancestral inference of samples of DNA sequences with recombination" Journal of Computational Biology, vol. 3, No. 4 (1996) pp. 479-502.
Gudbjartsson, et al., "Allegro, a new computer program for multipoint linkage analysis" Nat. Genet. 25, (2000) pp. 12-13.
Guo, S., "Proportion of Genome Shared Identical by Descent by Relatives: Concept, Computation, and Applications" Am. J. Hum. Genet. 56 (1995) pp. 1468-1476.
Gusev, et al., "Whole population, genome-wide mapping of hidden relatedness," Genome Research, vol. 19, 2009, pp. 318-326.
Hajnal, J., "Concepts of random mating and the frequency of consanguineous marriages," Proceedings of the Royal Society of London. Series B. Biological Sciences 159, No. 974 (1963) pp. 125-177.

(56) References Cited

OTHER PUBLICATIONS

Hardy, O.J., "Estimation of pairwise relatedness between individuals and characterization of isolation-by-distance processes using dominant genetic markers" Molecular Ecology, 12 (2003) pp. 1577-1588.
Harris, D.L., "Genotypic covariances between inbred relatives" Genetics 50, (1964) pp. 1319-1348.
Hayward, et al., "Fibrillin-1 mutations in Marfan syndrome and other type-1 fibrillinopathies" Hum. Mutat. 10 (1997) pp. 415-423.
Heath, et al., "A novel approach to search for identity by descent in small samples of patients and controls from the same Mendelian breeding unit: a pilot study in myopia" Human Heredity, vol. 52, Feb. 2001, pp. 183-190.
Henn, B.M., et al. "Cryptic Distant Relatives Are Common in Both Isolated and Cosmopolitan Genetic Samples," PLosOne, vol. 7, No. 4, Apr. 3, 2012, pp. 1-3. <doi:10.1371/journal.pone.0034267>.
Hepler, A.B., "Improving forensic identification using Bayesian Networks and Relatedness Estimation" Ph.D Thesis, NCSU, Raleigh (2005) pp. 1-131.
Hernández-Sánchez, et al., "On the prediction of simultaneous inbreeding coefficients at multiple loci" Genet. Res. 83 (2004) pp. 113-120.
Hernández-Sánchez, et al., "Prediction of IBD based on population history for fine gene mapping" Genet. Sel. Evol. 38 (2006) pp. 231-252.
Heyer, et al., "Variability of the genetic contribution of Quebec population founders associated to some deleterious genes" Am. J. Hum. Genet. 56 (1995) pp. 970-978.
Hill, et al. "Prediction of multilocus identity-by-descent" Genetics 176, Aug. 2007, pp. 2307-2315.
Hill, et al., "Linkage disequilibrium in finite populations" Theor. Appl. Genet. 38, (1968) pp. 226-231.
Hill, et al., "Prediction of multi-locus inbreeding coefficients and relation to linkage disequilibrium in random mating populations" Theor Popul Biol. Sep. 2007, 72(2), pp. 179-185. <doi:10.1016/j.tpb.2006.05.006>.
Hill, et al., "Variances and covariances of squared linkage disequilibria in finite populations" Theor. Pop. Biol., 33 (1988) pp. 54-78. [PubMed: 3376052].
Hill, W.G., "Disequilibrium among several linked neutral genes in finite population. II Variances and covariances of disequilibria" Theor. Pop. Biol., vol. 6, 1974, pp. 184-198.
Hinrichs, et al., "Multipoint identity-by-descent computations for single-point polymorphism and microsatellite maps," BMC Genet. 6, Dec. 30, 2005, S34. <doi: 10.1186/1471-2156-6-S1-S34>.
Houwen, et al., "Genomic screening by searching for shared segments: mapping a gene for benign recurrent intrahepatic cholestasis" Nature Genetics vol. 8, Dec. 1994, pp. 380-386.
Howie, et al., "A Flexible and Accurate Genotype Imputation Method for the Next Generation of Genome-Wide Association Studies," PLoS Genetics, vol. 5, No. 6, Jun. 2009, pp. 1-15.
Howie, et al., "Fast and accurate genotype imputation in genome-wide association studies through pre-phasing," Nature Genetics, vol. 44, No. 8, Aug. 2012, pp. 955-960.
Hu, X.S., "Estimating the correlation of pairwise relatedness along chromosomes" Heredity 94, (2004) pp. 338-346. [PubMed: 15354191].
Huang, et al. "Whole genome DNA copy number changes identified by high density oligonucleotide arrays," Hum. Genomics vol. 1, No. 4, May 2004, pp. 287-299.
Huang, et al., "Ignoring linkage disequilibrium among tightly linked markers induces false-positive evidence of linkage for affected sib pair analysis" Am. J. Hum. Genet. 75, (2004) pp. 1106-1112.
Idury, et al., "A faster and more general hidden Markov model algorithm for multipoint likelihood calculations" Hum. Hered. 47(1997) pp. 197-202.
Jacquard, A., "Genetic information given by a relative" Biometrics, 28, (1972) pp. 1101-1114.
Jones, et al., "Methods of parentage analysis in natural populations" Molecular Ecology 12 (2003) pp. 2511-2523.

Karigl, G., "A recursive algorithm for the calculation of identity coefficients" Ann. Hum. Genet. 45, (1981) pp. 299-305.
Keith, J.M., et al., "Calculation of IBD Probabilities with Dense SNP or Sequence Data" Genetic Epidemiology 32 (2008) pp. 513-519.
Kent, J.W. "BLAT—The BLAST-Like Alignment Tool" Genome Res. 2002, vol. 12, pp. 656-664.
Kimmel, et al., "A block-free hidden Markov model for genotypes and its application to disease association" J. Comput. Biol. 12, (2005a) pp. 1243-1260.
Kimmel, et al., "GERBIL: genotype resolution and block identification using likelihood" Proc. Natl. Acad. Sci. USA 102, (2005b) pp. 158-162.
Kong, A. et al., "Detection of sharing by descent, long-range phasing and haplotype imputation," Nature Genetics, vol. 40, No. 9, Sep. 2008, pp. 1068-1075.
Kong, et al., "A combined linkage-physical map of the human genome," Am. J. Hum. Genet., vol. 75, 2004, pp. 1143-1148.
Kong, et al., "A high-resolution recombination map of the human genome" Nature Genetics, vol. 31, Jul. 2002, pp. 241-247.
Kong, et al., "Allele-sharing models—LOD scores and accurate linkage tests" Am. J. Hum. Genet. 61, (1997) pp. 1179-1188.
Kruglyak, et al., "Complete Multipoint Sib-Pair Analysis of Qualitative and Quantitative Traits" Am. J. Hum. Genet. 57, (1995) pp. 439-454.
Kruglyak, et al., "Faster multipoint linkage analysis using Fourier transforms" J. Comput. Biol. 5, (1998) pp. 1-7.
Kruglyak, et al., "Linkage thresholds for two-stage genome scans" Am. J. Hum. Genet. 62, (1998) pp. 994-997.
Kruglyak, et al., "Parametric and Nonparametric Linkage Analysis: A Unified Multipoint Approach" Am. J. Hum. Genet. 58, (1996) pp. 1347-1363.
Kruglyak, et al., "Rapid Multipoint Linkage Analysis of Recessive Traits in Nuclear Families, Including Homozygosity Mapping" Am. J. Hum. Genet. 56 (1995) pp. 519-527.
Kruglyak, L., "The use of a genetic map of biallelic markers in linkage studies" Nat. Genet. 17, (1997) pp. 21-24.
Kumar, et al., "Recurrent 16p11.2 microdeletions in autism" Human Molecular Genetics, 2008, vol. 17, No. 4, pp. 628-638.
Laberge, et al., "Population history and its impact on medical genetics in Quebec" Clin. Genet. 68 (2005) pp. 287-301.
Lafrate, et al., "Detection of large-scale variation in the human genome," Nature Genetics, vol. 36, No. 9, Sep. 2004, pp. 949-951.
Lander, et al., "Construction of multilocus genetic linkage maps in humans" Genetics, vol. 84, Apr. 1987, pp. 2363-2367.
Lander, et al., "Genetic dissection of complex traits: guidelines for interpreting and reporting linkage results" Nat. Genet. 11, (1995) pp. 241-247.
Lander, et al., "Homozygosity mapping: a way to map human recessive traits with the DNA of inbred children" Science 236, (1987) pp. 1567-1570.
Lange, et al., "Extensions to pedigree analysis I. Likelihood calculations for simple and complex pedigrees" Hum. Hered. 25 (1975) pp. 95-105.
Leclair, et al., "Enhanced kinship analysis and STR-based DNA typing for human identification in mass fatality incidents: The Swissair Flight 111 disaster" Journal of Forensic Sciences, 49(5) (2004) pp. 939-953.
Leibon, et al., "A simple computational method for the identification of disease-associated loci in complex, incomplete pedigrees" arXiv:0710:5625v1 [q-bio.GN] Oct. 30, 2007, pp. 1-20.
Leibon, et al.,"A SNP Streak Model for the Identification of Genetic Regions Identical-by-descent" Statistical Applications in Genetics and Molecular Biology, vol. No. 1, Article 16 (2008) pp. 1-17.
Leutenegger, et al., "Estimation of the Inbreeding Coefficient through Use of Genomic Data," Am. J. Hum. Genet. 73, Jul. 29, 2003, pp. 516-523.
Leutenegger, et al., "Using genomic inbreeding coefficient estimates for homozygosity mapping of rare recessive traits: Application to Taybi-Linder syndrome" Am. J. Hum. Genet., vol. 79, Jul. 2006, pp. 62-66.

(56) References Cited

OTHER PUBLICATIONS

Li, et al., "Fast and accurate long-read alignment with Burrows-Wheeler transform" Bioinformatics vol. 26, No. 5, 2010, pp. 589-595.
Li, et al., "Joint modeling of linkage and association: identifying SNPs responsible for a linkage signal" Am. J. Hum. Genet. 76 (2005) pp. 934-949.
Li, et al., "Mapping short DNA sequencing reads and calling variants using mapping quality scores," Genome Research, Aug. 19, 2008, pp. 1851-1858. <doi:10.1101/gr.078212.108>.
Li, et al., "Modeling linkage disequilibrium and identifying recombination hotspots using single-nucleotide polymorphism data" Genetics 165, (2003) pp. 2213-2233.
Li, et al., "Similarity of DNA fingerprints due to chance and relatedness" Hum. Hered. 43, 1993 pp. 45-52.
Li, et al., "The sequence alignment/map format and SAMtools" Bioinformatics vol. 25, No. 16 (2009) pp. 2078-2079.
Lien, et al. "Evidence for heterogeneity in recombination in the human pseudoautosomal region: High resolution analysis by sperm typing and radiation-hybrid mapping" Am. J. Hum. Genet. 66, 2000, pp. 557-566.
Lin, et al. "Haplotype inference in random population samples" Am. J. Hum. Genet. 71, 2002, pp. 1129-1137.
Liu, et al., "Affected sib-pair test in inbred populations" Ann. Hum. Genet. 68, (2004) pp. 606-619.
Long, et al., "An E-M Algorithm and Testing Strategy for Multiple-Locus Haplotypes" Am. J. Hum. Genet. 56 (1995) pp. 799-810.
Lowe, et al., "Genome-Wide Association Studies in an Isolated Founder Population from the Pacific Island of Kosrae," PLoS Genet 5(2), 2009, e1000365, pp. 1-17. <doi:10.1371/journal.pgen.1000365>.
Lynch, et al., "Analysis of population genetic structure with RAPD markers" Molecular Ecology, 3, (1994) pp. 91-99.
Lynch, et al., "Estimation of pairwise relatedness with molecular markers" Genetics, vol. 152, (1999) pp. 1753-1766.
Lynch, M., "Estimation of relatedness by DNA fingerprinting" Molecular and Biological Evolution, 5, (1988) pp. 584-599.
Ma, et al., "PatternHunter: faster and more sensitive homology search" Bioinformatics, vol. 18, No. 3 (2002) pp. 440-445.
Mao, et al., "A Monte Carlo algorithm for computing the IBD matrices using incomplete marker information" Heredity (2005) 94, pp. 305-315.
Marchini, et al., "A comparison of phasing algorithms for trios and unrelated individuals," Am. J. Hum. Genet. 78, 2006, pp. 437-450.
Matsuzaki, et al., "Genotyping over 100,000 SNPs on a pair of oligonucleotide arrays" Nat. Methods, vol. 1, No. 2, Nov. 2004, pp. 109-111.
Matsuzaki, et al., "Parallel genotyping of over 10,000 SNPs using a one-primer assay on a high-density oligonucleotide array" Genome Res., vol. 14, No. 3, Mar. 2004, pp. 414-425.
McPeek, et al., "Statistical test for detection of misspecified relationships by use of genome-screen data" Am. J. Hum. Genet. 66, (2000) pp. 1076-1094.
Meuwissen, et al., "Fine mapping of a quantitative trait locus for twinning rate using combined linkage and linkage disequilibiium mapping," Genetics 161 (2002) pp. 373-379.
Meuwissen, et al., "Multipoint Identity-by-Descent Prediction Using Dense Markers to Map Quantitative Trait Loci and Estimate Effective Population Size," Genetics 176, Aug. 2007, pp. 2551-2560.
Meuwissen, et al., "Prediction of identity by descent probabilities from marker-haplotypes," Genetics Selelction Evolution, vol. 33, Nov. 15, 2001, pp. 605-634. <doi: 10.1186/1297-9686-33-6-605>.
Miano, et al., "Pitfalls in homozygosity mapping" Am. J. Hum. Genet. 67, (2000) pp. 1348-1351.
Milligan, B.G., "Maximum-Likelihood Estimation of Relatedness" Genetics 163, (2003) pp. 1153-1167.
Miyazawa et al., "Homozygosity Haplotype Allows a Genomewide Search for the Autosomal Segments Shared among Patients," Am. J. Hum. Genet. vol. 80, Jun. 2007, pp. 1090-1102.
Morris, et al., "The avuncular index and the incest index" Advances in Forensic Haemogenetics 2, (1988) pp. 607-611.
Morton, N. E., "Sequential test for the detection of linkage" Am. J. Hum. Genet. 7 (1955) pp. 277-318.
Motro, et al., "The affected sib method. I. Statistical features of the affected sib-pair method" Genetics 110, (1985) pp. 525-538.
Nelson, et al., "Genomic mismatch scanning. A new approach to genetic linkage mapping" Nature Genetics, vol. 4, May 1993, pp. 11-18.
Newton, et al., "Inferring the location and effect of tumor suppressor genes by instability-selection modeling of allelic-loss data" Biometrics 56, (2000) pp. 1088-1097.
Newton, et al., "On the statistical analysis of allelic-loss data" Statistics in Medicine 17, (1998) pp. 1425-1445.
Ning et al., "SSAHA: A Fast Search Method for Large DNA Databases," Genome Research, Oct. 2001, vol. 11, No. 10, pp. 1725-1729.
Nyholt, Dale R., "GENEHUNTER: Your 'One-Stop Shop' for Statistical Genetic Analysis?" Hum. Hered. 53 (2002) pp. 2-7.
O'Connell, J.R., "Rapid multipoint linkage analysis via inheritance vectors in the Elston-Stewart algorithm" Hum. Hered. 51, (2001) pp. 226-240.
O'Connell, J.R., "The VITESSE algorithm for rapid exact multilocus linkage analysis via genotype set-recoding and fuzzy inheritance" Nature. Genet. 11, (1995) pp. 402-408.
Oliehoek, et al., "Estimating relatedness between individuals in general populations with a focus on their use in conservation programs" Genetics 173 (2006) pp. 483-496.
Olson, et al., "Relationship estimation by Markov-process models in sib-pair linkage study" Am. J. Hum. Genet. 64, (1999) pp. 1464-1472.
Opposition to Defendants' Motion to Dismiss Plaintiff's Complaint, filed in the United States District Court in and for the Northern District of California LLC on Jul. 13, 2018, Case No. 18-cv-02791-JCS, Re *23andMe, Inc. v. Ancestry.com DNA, LLC, Ancestry.com Operations Inc., and Ancestry.com*.
Order Granting in Part and Denying in Part Defendants' Motion to Dismiss, dated Aug. 23, 2018, Case No. 18-cv-02791-JCS, from the United States District Court in and for the Northern District of California LLC, Re *23andMe, Inc. v. Ancestry.com DNA, LLC, Ancestry.com Operations Inc., and Ancestry.com*.
Patterson, et al., "Population Structure and Eigenanalysis," PLoS Genetics, vol. 2, No. 12, e190, Dec. 2006, pp. 2074-2093.
Paynter, et al., "Accuracy of Multiplexed Illumina Platform-Based Single-Nucleotide Polymorphism Genotyping Compared between Genomic and Whole Genome Amplified DNA Collected from Multiple Sources," Cancer Epidemiol Biomarkers Prev. 15, Dec. 2006, pp. 2533-2536.
Pemberton et al., "Inference of unexpected Genetic relatedness among individuals in HapMap phase III" Am. J. Hum. Genet. 87, (2010) pp. 457-464.
Perry, et al., "The fine-scale and complex architecture of human copy-number variation," Am. J. Hum. Genet. 82, Mar. 2008, pp. 685-695.
Pinto, et al., "Copy-number variation in control population cohorts," Human Molecular Genetics, 2007, vol. 16, review issue No. 2, pp. R168-R173. <doi:10.1093/hmg/ddm241>.
Porras-Hurtado, et al., "An overview of STRUCTURE: applications, parameter settings, and supporting software," Frontiers in Genetics, vol. 4, No. 96, May 29, 2013, pp. 1-13.
Pritchard, et al., "Association Mapping in Structured Populations," Am. J. Hum. Genet., vol. 67, 2000, pp. 170-181.
Pritchard, et al., "Inference of population structure using multilocus genotype data" Genetics 155, (2000) pp. 945-959.
Purcell, et al., "PLINK: A Tool Set for Whole-Genome Association and Population-Based Linkage Analysis," The American Journal of Human Genetics, vol. 81, Sep. 2007, pp. 559-575.
Queller, et al., "Estimating relatedness using genetic markers" Evolution, vol. 43, No. 2, (1989) pp. 258-275.
Rabiner, L., "A Tutorial on Hidden Markov Models and Selected Applications in Speech Recognition," Proceedings of the IEEE, vol. 77, No. 2, Feb. 1989, pp. 257-286.

(56) References Cited

OTHER PUBLICATIONS

Rannala, et al., "Detecting immigration by using multilocus genotypes" Proc. Natl. Acad. Sci. USA 94, (1997) pp. 9197-9201.
Rastas, et al., "A hidden Markov technique for haplotype reconstruction" Lect. Notes Comput. Sci. 3692, (2005) pp. 140-151.
Redon, et al., "Global variation in copy number in the human genome," Nature vol. 444, Nov. 23, 2006, pp. 444-454. <doi:10.1038/nature05329>.
Reid, et al., "Specificity of sibship determination using the ABI identifier multiplex system" J. Forensic Sci. 49, (2004) pp. 1262-1264.
Reply Brief of Appellant 23AndMe, Inc., Case No. 2019-1222, Document: 25, Filed on Apr. 8, 2019, in the US Court of Appeals for Federal Circuit, pp. 1-38.
Riquet, J. et al., "Fine-mapping of quantitative trait loci by identity by descent in outbred populations: application to milk production in dairy cattle," Proceedings of the National Academy of Sciences, vol. 96, No. 16, Aug. 3, 1999, pp. 9252-9257. <doi: 10.1073/pnas.96.16.9252>.
Risch, et al., "Linkage strategies for genetically complex traits. II. The power of affected relative pairs" Am. J. Hum. Genet. 46 (1990) pp. 229-241.
Risch, N., "Linkage Strategies for Genetically Complex Traits. II. The Power of Affected Relative Pairs" Am. J. Hum. Genet. 46, (1990 a,b) pp. 222-241.
Ritland, et al., "Inferences about quantitative inheritance based on natural population structure in the yellow monkeyflower, *Mimulus guttatus*" Evolution 50, (1996) pp. 1074-1082.
Ritland, K., "A marker-based method for inferences about quantitative inheritance in natural populations" Evolution 50, (1996b) pp. 1062-1073.
Ritland, K., "Estimators for pairwise relatedness and individual inbreeding coefficients" Genet. Res. 67 (1996a) pp. 175-185.
Ritland, K., "Marker-inferred relatedness as a tool for detecting heritability in nature" Mol. Ecol. 9, (2000) pp. 1195-1204.
Sanda, et al., "Genomic analysis I: inheritance units and genetic selection in the rapid discovery of locus linked DNA makers" Nucleic Acids Research, vol. 14, No. 18 (1986) pp. 7265-7283.
Schaid, et al., "Caution on pedigree haplotype inference with software that assumes linkage equilibrium" Am. J. Hum. Genet. 71, (2002) pp. 992-995.
Scheet, et al., "A Fast and Flexible Statistical Model for Large-Scale Population Genotype Data: Applications to Inferring Missing Genotypes and Haplotypic Phase," The American Journal of Human Genetics, vol. 78, Apr. 2006, pp. 629-644.
Schork, N.J., "Extended Multipoint Identity-by-Descent Analysis of Human Quantitative Traits: Efficiency, Power, and Modeling Considerations" Am. J. Hum. Genet. 53 (1993) pp. 1306-1319.
Shmulewitz, et al., "Linkage analysis of quantitative traits for obesity, diabetes, hypertension, and dyslipidemia on the island of Kosrae, Federated States of Micronesia," Proc. Natl. Acad. Sci. vol. 103, No. 10, Mar. 7, 2006, pp. 3502-3509.
Shore, et al., "A recurrent mutation in the BMP type I receptor ACVR1 causes inherited and sporadic fibrodysplasia ossificans progressiva" Nat. Genet. 38 (2006) pp. 525-527.
Siegmund, et al., "Statistical Analysis of Direct Identity-by-descent Mapping," Annals of Human Genetics (2003) 67,464-470.
Slager, et al., "Evaluation of candidate genes in case-control studies: a statistical method to account for related subjects" Am. J. Hum. Genet. 68, (2001) pp. 1457-1462.
Smouse, et al., "A genetic mixture analysis for use with incomplete source population data" Can J Fisheries Aquatic Sci. 47 (1990) pp. 620-634.
Sobel, et al., "Descent graphs in pedigree analysis: Applications to haplotyping, location scores, and marker-sharing statistics" Am. J. Hum. Genet. 58, (1996) pp. 1323-1337.
Stam, P., "The distribution of the fraction of the genome identical by descent in finite random mating populations" Genet. Res. Camb. 35, (1980) pp. 131-155.

Stephens, et al., "A Comparison of Bayesian Methods for Haplotype Reconstruction from Population Genotype Data," Am. J. Hum. Genet., vol. 73, 2003, pp. 1162-1169.
Stephens, et al., "A New Statistical Method for Haplotype Reconstruction from Population Data," Am. J. Hum. Genet., vol. 68, 2001, pp. 978-989.
Stephens, et al., "Accounting for Decay of Linkage Disequilibrium in Haplotype Inference and Missing-Data Imputation," Am. J. Hum. Genet., vol. 76, 2005, pp. 449-462.
Stone, et al., "DELRIOUS: a computer program designed to analyze molecular marker data and calculate delta and relatedness estimates with confidence" Molecular Ecology Notes, vol. 1, (2001) pp. 209-212.
Tang, et al., "Estimation of individual admixture: Analytical and study design considerations" Genet. Epidem. 28, (2005) pp. 289-301.
Te Meerman, et al., "Genomic Sharing Surrounding Alleles Identical by Descent: Effects of Genetic Drift and Population Growth" Genetic Epidemiology vol. 14 (1997) pp. 1125-1130.
Teo, et al., "Singapore Genome Variation Project: A haplotype map of three Southeast Asian populations" Genome Res. 19, (2009) pp. 2154-2162.
The International HapMap Consortium, "A haplotype map of the human genome" vol. 437, Oct. 27, 2005, pp. 1300-1320. <doi:10.1038/nature04226>.
The International HapMap Consortium, "A haplotype map of the human genome," Nature, vol. 437, Oct. 27, 2005, pp. 1299-1320. <doi:10.1038/nature04226>.
The International HapMap Consortium, "A second generation human haplotype map of over 3.1 million SNPs," Nature, vol. 449, Oct. 18, 2007, pp. 851-860. <doi:10.1038/nature06258>.
Thomas, et al., "Genomic mismatch scanning in pedigrees" IMA Journal of Mathematics Applied in Medicine and Biology, vol. 11, (1994) pp. 1-16.
Thomas, et al., "Multilocus linkage analysis by blocked Gibbs sampling" Statistics and Computing, vol. 10, (2000), pp. 259-269.
Thomas, et al., "Shared genomic segment analysis. Mapping disease predisposition genes in extended pedigrees using SNP genotype assays," Ann. Hum. Genet. 72, Mar. 2008, pp. 279-287.
Thompson, E.A., "Estimation of relationships from genetic data" In Handbook of Statistics, vol. 8, (1991) pp. 255-269.
Thompson, E.A., "Inference of genealogical structure" Soc. Sci. Inform. 15, (1976) pp. 477-526.
Thompson, E.A., "The estimation of pairwise relationships" Ann. Hum. Genet., Lond. 39, (1975) pp. 173-188.
Thompson, et al., "The IBD process along four chromosomes," Theor. Popul. Biol. May 73(3) May 2008, pp. 369-373.
Tishkoff, et al., "The Genetic Structure and History of Africans and African Americans," Science, vol. 324(5930), May 22, 2009, pp. 1035-1044. <doi:10.1126/science.1172257>.
Todorov, et al., "Probabilities of identity-by-descent patterns in sibships when the parents are not genotyped" Genet. Epidemiol. 14 (1997) pp. 909-913.
Transcript of Proceedings dated Aug. 16, 2018, Case No. 18-cv-02791-JCS, Re Defendant's Motion to Dismiss, heard in the United States District Court in and for the Northern District of California LLC, in the matter of *23andMe, Inc. v. Ancestry.com DNA, LLC, Ancestry.com Operations Inc., and Ancestry.com*.
Tu, et al., "The maximum of a function of a Markov chain and application to linkage analysis" Adv. Appl. Probab. 31, (1999) pp. 510-531.
Tzeng, et al., "Determination of sibship by PCR-amplified short tandem repeat analysis in Taiwan" Transfusion 40, (2000) pp. 840-845.
Van De Casteele, et al., "A comparison of microsatellite-based pairwise relatedness estimators" Molecular Ecology 10, (2001) pp. 1539-1549.
Wang, et al., "An estimator of pairwise relatedness using molecular markers" Genetics, vol. 160 (2002) pp. 1203-1215.
Wang, et al., "An integrated hidden Markov model designed for high-resolution copy number variation detection in whole-genome SNP genotyping data," Genome Res. 17, 2007, pp. 665-1674.

(56) References Cited

OTHER PUBLICATIONS

Weir, et al., "A maximum-likelihood method for the estimation of pairwise relatedness in structured populations" Genetics 176, (2007) pp. 421-440.
Weir, et al., "Allelic association patterns for a dense SNP map" Genetic Epidemiology 24, (2004) pp. 442-450.
Weir, et al., "Behavior of pairs of loci in finite monoecious populations" Theor. Popul. Biol. 6 (1974) pp. 323-354.
Weir, et al., "Estimating F-statistics" Annual Review of Genetics, 36, (2002) pp. 721-750.
Weir, et al., "Genetic relatedness analysis: modern data and new challenges" Nature Genetics 7, (2006) pp. 771-780.
Weir, et al., "Group inbreeding with two linked loci" Genetics 63 (1969) pp. 711-742.
Weir, et al., "Measures of human population structure show heterogeneity among genomic regions" Genome Res. 15 (2005) pp. 1468-1476. [PubMed:16251456].
Weiss, et al., "Association between microdeletion and microduplication at 16p11.2 and autism" New England Journal of Medicine, vol. 358, No. 7, Feb. 14, 2008, pp. 667-675.
Whittemore, et al., "A Class of Tests for Linkage Using Affected Pedigree Members" Biometrics 50, (1994) pp. 118-127.
Wijsman, et al., "Multipoint linkage analysis with many multiallelic or dense diallelic markers: Markov chain-Monte Carlo provides practical approaches for genome scans on general pedigrees" Am. J. Hum. Genet. 79, (2006) pp. 846-858.
Wright, S. "Systems of Mating. I. The Biometric Relations Between Parent and Offspring," Genetics, 6:111.
Yu, et al., "A unified mixed-model method for association mapping accounting for multiple levels of relatedness" Nature Genet. 38, (2006) pp. 203-208.
Zhang, et al., "A comparison of several methods for haplotype frequency estimation and haplotype reconstruction for tightly linked markers from general pedigrees" Genet. Epidemiol. 30 (2006) pp. 423-437.
Zhao et al., "On Relationship Inference Using Gamete Identity by Descent Data", Journal of Computational Biology, vol. 8, No. 2, Nov. 2, 2001, pp. 191-200.
U.S. Appl. No. 12/774,546, filed May 5, 2010, Machpherson et al.
Office Action dated Jan. 3, 2014 in U.S. Appl. No. 12/774,546.
Final Office Action dated Jan. 8, 2015 in U.S. Appl. No. 12/774,546.
Office Action dated Aug. 12, 2015 in U.S. Appl. No. 12/774,546.
Final Office Action dated Feb. 2, 2016 in U.S. Appl. No. 12/774,546.
Office Action dated Feb. 1, 2017 in U.S. Appl. No. 12/774,546.
EP Examination Report issued in Application No. 17172048.5 dated Apr. 21, 2020.
Hon, et al., "Discovering Distant Relatives within a Diverse Set of Populations Using DNA Segments Identical by Descent" *Advancing Human Genetics & Genomics Annual Meeting Poster Session*, Oct. 20, 2009, 23andMe, Inc., pp. 1-2.
*23andMe, Inc., v. Ancestry.com DNA, LLC, Ancestry.com Operations Inc., Ancestry.com LLC*, No. 2019-1222, United States Court of Appeals for the Federal Circuit, *Petition for Rehearing En Banc*, filed Nov. 4, 2019, Case No. 18-cv-02791-EMC, pp. 1-28.
*23andMe, Inc., v. Ancestry.com DNA, LLC, Ancestry.com Operations Inc., Ancestry.com LLC*, No. 2019-1222, United States Court of Appeals for the Federal Circuit, *Defendant's-Appellees' Response to Appellant 23ANDME, INC.'S Petition for Rehearing En Banc*, filed Dec. 19, 2019, Case No. 18-cv-02791-EMC, pp. 1-25.
*23andMe, Inc., v. Ancestry.com DNA, LLC, Ancestry.com Operations Inc., Ancestry.com LLC*, No. 2019-1222, United States Court of Appeals for the Federal Circuit, *On Petition for Rehearing En Banc ; Order, denied*; filed Jan. 9, 2020, Case No. 18-cv-02791-EMC, pp. 1-2.
U.S. Final Office Action dated Dec. 19, 2011 in U.S. Appl. No. 12/288,096.
U.S. Office Action dated Jul. 21, 2011 in U.S. Appl. No. 12/288,096.
U.S. Office Action dated Jun. 13, 2013 in U.S. Appl. No. 12/288,096.
U.S. Office Action dated Dec. 19, 2013 in U.S. Appl. No. 12/288,096.
U.S. Office Action dated Aug. 6, 2014 in U.S. Appl. No. 12/288,096.
U.S. Final Office Action dated Mar. 19, 2015 in U.S. Appl. No. 12/288,096.
U.S. Office Action dated Jul. 22, 2015 in U.S. Appl. No. 12/288,096.
U.S. Final Office Action dated Jan. 11, 2016 in U.S. Appl. No. 12/288,096.
U.S. Office Action dated Sep. 9, 2016 in U.S. Appl. No. 12/288,096.
U.S. Final Office Action dated Apr. 28, 2017 in U.S. Appl. No. 12/288,096.
U.S. Office Action dated Mar. 13, 2018 in U.S. Appl. No. 12/288,096.
U.S. Notice of Allowance dated Nov. 26, 2018 in U.S. Appl. No. 12/288,096.
U.S. Office Action dated Sep. 17, 2019 in U.S. Appl. No. 16/409,574.
U.S. Notice of Allowance dated Jan. 3, 2020 in U.S. Appl. No. 16/409,574.
U.S. Office Action dated Jul. 21, 2011 in U.S. Appl. No. 12/288,026.
U.S. Final Office Action dated Dec. 19, 2011 in U.S. Appl. No. 12/288,026.
U.S. Office Action dated Oct. 2, 2013 in U.S. Appl. No. 12/288,026.
U.S. Final Office Action dated Apr. 16, 2014 in U.S. Appl. No. 12/288,026.
U.S. Office Action dated Dec. 4, 2014 in U.S. Appl. No. 12/288,026.
U.S. Final Office Action dated May 22, 2015 in U.S. Appl. No. 12/288,026.
U.S. Office Action dated Sep. 9, 2016 in U.S. Appl. No. 12/288,026.
U.S. Final Office Action dated Apr. 27, 2017 in U.S. Appl. No. 12/288,026.
Notice of Allowance dated Sep. 12, 2017 in U.S. Appl. No. 12/288,026.
U.S. Office Action dated Jun. 23, 2020 in U.S. Appl. No. 15/829,782.
International Search Report and Written Opinion dated Dec. 10, 2008 in PCT/US2008/11806.
International Preliminary Report on Patentability dated Apr. 29, 2010 in PCT/US2008/011806.
International Search Report and Written Opinion dated Dec. 29, 2008 in PCT/US2008/11833.
International Preliminary Report on Patentability dated Apr. 20, 2010 in PCT/US2008/011833.
Avalos, et al. "Mendelian Inheritance" Encyclopedia of Molecular Biology (2002) pp. 1-4, John Wiley and Sons Inc. ebook. [retrieved Jun. 18, 2020].
PubMed.gov Overview. Downloaded from Pubmed.gov Jun. 18, 2020. eResource. 1 page.
Pearson, W. R., et al. "Improved tools for biological sequence comparison," Proceedings of the National Academy of Sciences (PNAS), Biochemistry, vol. 85, No. 8, Apr. 1, 1988, pp. 2444-2448.
Human Genome Landmarks Poster, United States Department of Energy (DOE), pp. 6. [retrieved on Jan. 27, 2007] <URL:http//web.archive.org/web/20070127170426/http://www.ornl.gov/sci/techresources/Human_Genome/posters/chromosome/chooser.shtml>.
Yang, et al., "LINKERS: A simulation programming system for generating populations with genetic structure" Computers in Biology and Medicine, vol. 20, No. 2, 1990, pp. 135-144.
Osier, et al., "ALFRED: An allele frequency database for anthropology," American Journal of Physical Anthropology, vol. 119, No. 1, Aug. 14, 2002, pp. 77-83. <doi:10.1002/ajpa.10094>.
Poznik, et al., "A novel framework for sib pair linkage analysis," The American Journal Human Genetics, vol. 78, Feb. 2006, pp. 222-230.
Purcell, et al., "PLINK: A Tool Set for Whole-Genome Association and Population-Based Linkage Analyses," The American Journal of Human Genetics, vol. 81, Sep. 2007, pp. 559-575.
Rao, et al., "SAGE Programs; Model free linkage analysis for complex cardiovascular phentyopes," Methods in Molecular Medicine, vol. 128, chapter 6, (2006) pp. 61-89.
U.S. Appl. No. 17/073,110, filed Oct. 16, 2020, Hon et al.
U.S. Appl. No. 17/073,122, filed Oct. 16, 2020, Hon et al.
U.S. Appl. No. 17/073,128, filed Oct. 16, 2020, Hon et al.
U.S. Appl. No. 17/077,930, filed Oct. 22, 2020, Macpherson et al.
Notice of Allowance dated Jan. 7, 2021 in U.S. Appl. No. 17/073,110.
Office Action dated Dec. 24, 2020 in U.S. Appl. No. 17/073,122.
Office Action dated Dec. 21, 2020 in U.S. Appl. No. 17/077,930.

(56) References Cited

OTHER PUBLICATIONS

Office Action dated Feb. 3, 2021 in U.S. Appl. No. 17/073,128.

* cited by examiner

| CONTACT STATUS | PREDICTED RELATIONSHIP | RELATIONSHIP RANGE | PERSONAL DETAILS | % DNA SHARED | # SHARED SEGMENTS |
|---|---|---|---|---|---|
| MAKE CONTACT | 4TH COUSIN | 4TH TO 10TH COUSIN | FEMALE MATERNAL HAPLOGROUP F3 | 0.19% | 2 |
| MAKE CONTACT | 5TH COUSIN | 3RD TO 10TH COUSIN | FEMALE CENTRAL ASIAN ANCESTRY MATERNAL HAPLOGROUP G | 0.12% | 1 |
| MAKE CONTACT | 5TH COUSIN | 3RD TO 10TH COUSIN | MALE MATERNAL HAPLOGROUP G1A PATERNAL HAPLOGROUP B1b1b2a1a2d | 0.11% | 1 |
| MAKE CONTACT | 5TH COUSIN | 4TH TO 10TH COUSIN | MALE MATERNAL HAPLOGROUP R9b PATERNAL HAPLOGROUP O3a3c | 0.10% | 1 |
| MAKE CONTACT | 5TH COUSIN | 4TH TO 10TH COUSIN | FEMALE MATERNAL HAPLOGROUP B | 0.09% | 1 |
| MAKE CONTACT | 5TH COUSIN | 4TH TO 10TH COUSIN | MALE MATERNAL HAPLOGROUP D4C1 PATERNAL HAPLOGROUP O3a | 0.09% | 1 |
| MAKE CONTACT | 5TH COUSIN | 4TH TO 10TH COUSIN | MALE MATERNAL HAPLOGROUP F1a1* PATERNAL HAPLOGROUP O1a1* | 0.09% | 1 |
| SHARING GENOMES SEND A MESSAGE | PARENT OR CHILD | -- | ****** MATERNAL HAPLOGROUP C | 50.11% | 24 |

FIG. 4C

| LIST VIEW | DISCOVERY VIEW | | | | |
|---|---|---|---|---|---|
| FILTER PREDICTED RELATIVES: ALL RESULTS (12) | | | | | RESULTS 1-12 OF 12 |
| PARENT OR CHILD | SIBLING | GRANDPARENT, GRANDCHILD, OR HALF-SIBLING | 4TH COUSIN | 5TH COUSIN | 7TH COUSIN |

MALE
MATERNAL HAPLOGROUP D4e1
PATERNAL HAPLOGROUP O3a

PREDICTED RELATIONSHIP: 5TH COUSIN
RELATIONSHIP RANGE: 4TH TO 10TH COUSIN

[ MAKE CONTACT ]

FOR MORE ABOUT RELATIV
✉ SEND FEEDBACK TO

FIG. 4D

| CONTACT STATUS | PREDICTED RELATIONSHIP | RELATIONSHIP RANGE | PERSONAL DETAILS | % DNA SHARED | # SHARED SEGMENTS |
|---|---|---|---|---|---|
| THIS PERSON WOULD LIKE TO CONTACT YOU. VIEW MESSAGE | AUNT/UNCLE NEPHEW, NIECE OR HALF-SLIBLING | -- | DANIEL LAWRENCE RF2_, MATERNAL HAPLOGROUP U5a1* PATERNAL HAPLOGROUP R1b1b2a1a2d3* | 20.22% | 43 |
| CONTACT ACCEPTED SEND A MESSAGE VIEW CONVERSATION | SIBLING | -- | ERIN LAWRENCE RF2_, MATERNAL HAPLOGROUP H1 | 46.75% | 29 |

FIG. 4H

```
Alice  A G T | C T G | C A A | ... -- 902
       C G A | C A G | T C A | ... -- 904

Bob    C A T | G A C | C C G | ... -- 906
       A A T | C T G | C A A | ... -- 908
```

FIG. 9

FINDING RELATIVES IN A DATABASE

INCORPORATION BY REFERENCE

An Application Data Sheet is filed concurrently with this specification as part of the present application. Each application that the present application claims benefit of or priority to as identified in the concurrently filed Application Data Sheet is incorporated by reference herein in its entirety and for all purposes.

BACKGROUND OF THE INVENTION

Genealogy is the study of the history of families and the line of descent from ancestors. It is an interesting subject studied by many professionals as well as hobbyists. Traditional genealogical study techniques typically involve constructing family trees based on surnames and historical records. As gene sequencing technology becomes more accessible, there has been growing interest in genetic ancestry testing in recent years.

Existing genetic ancestry testing techniques are typically based on deoxyribonucleic acid (DNA) information of the Y chromosome (Y-DNA) or DNA information of the mitochondria (mtDNA). Aside from a small amount of mutation, the Y-DNA is passed down unchanged from father to son and therefore is useful for testing patrilineal ancestry of a man. The mtDNA is passed down mostly unchanged from mother to children and therefore is useful for testing a person's matrilineal ancestry. These techniques are found to be effective for identifying individuals that are related many generations ago (e.g., 10 generations or more), but are typically less effective for identifying closer relationships. Further, many relationships that are not strictly patrilineal or matrilineal cannot be easily detected by the existing techniques.

BRIEF DESCRIPTION OF THE DRAWINGS

Various embodiments of the invention are disclosed in the following detailed description and the accompanying drawings.

FIGS. 4A-4I are screenshots illustrating user interface examples in connection with process 300.

FIG. 9 is a diagram illustrating an example in which phased data is compared to identify IBD.

DETAILED DESCRIPTION

Figure 1:
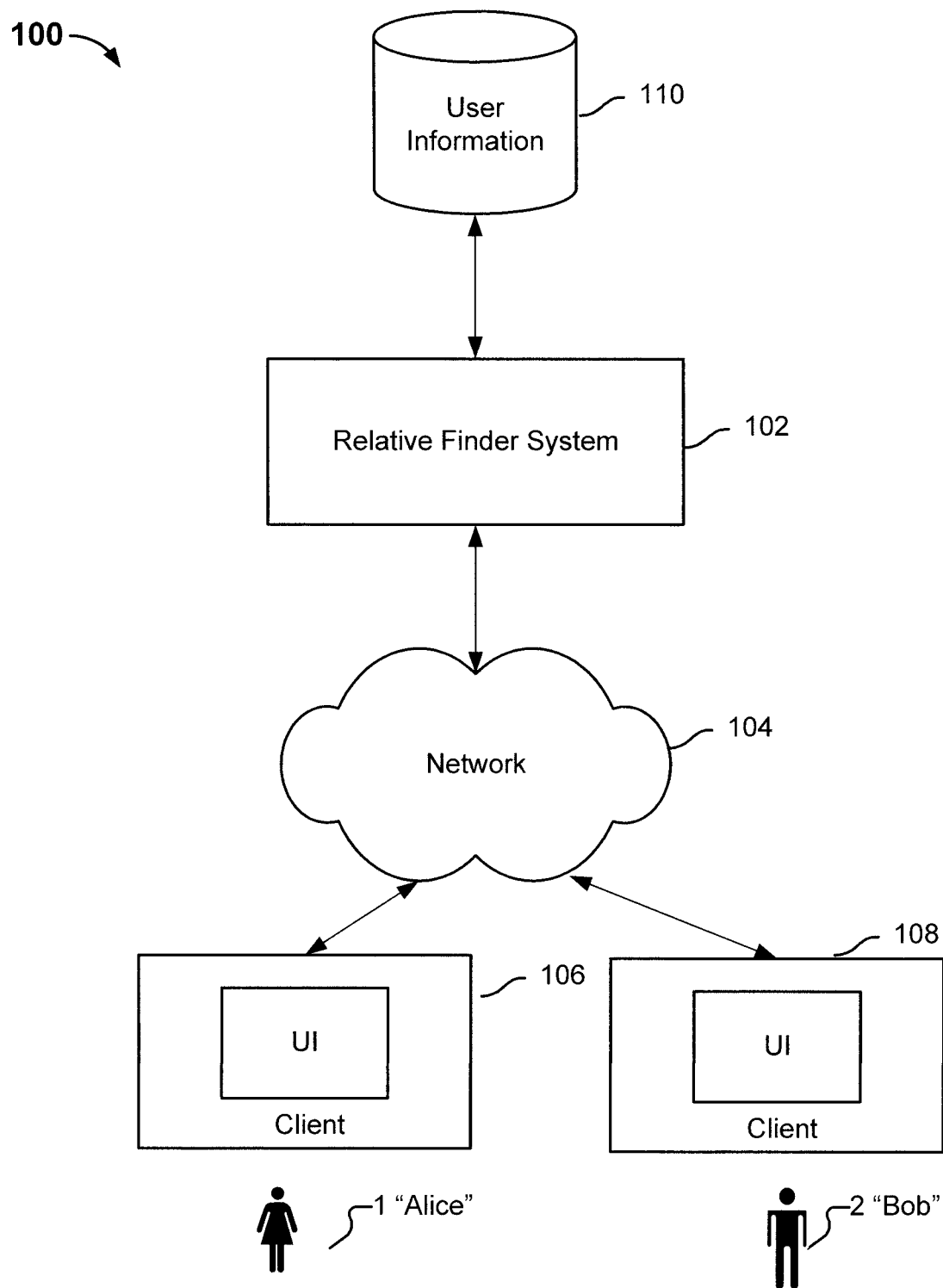
FIG. 1 is a block diagram illustrating an embodiment of a relative finding system.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Because of recombination and independent assortment of chromosomes, the autosomal DNA and X chromosome DNA (collectively referred to as recombinable DNA) from the parents is shuffled at the next generation, with small amounts of mutation. Thus, only relatives will share long stretches of genome regions where their recombinable DNA is completely or nearly identical. Such regions are referred to as "Identical by Descent" (IBD) regions because they arose from the same DNA sequences in an earlier generation. The relative finder technique described below is based at least in part on locating IBD regions in the recombinable chromosomes of individuals.

In some embodiments, locating IBD regions includes sequencing the entire genomes of the individuals and comparing the genome sequences. In some embodiments, locating IBD regions includes assaying a large number of markers that tend to vary in different individuals and comparing the markers. Examples of such markers include Single Nucleotide Polymorphisms (SNPs), which are points along the genome with two or more common variations; Short Tandem Repeats (STRs), which are repeated patterns of two or more repeated nucleotide sequences adjacent to each other; and Copy-Number Variants (CNVs), which include longer sequences of DNA that could be present in varying numbers in different individuals. Long stretches of DNA sequences from different individuals' genomes in which markers in the same locations are the same or at least compatible indicate that the rest of the sequences, although not assayed directly, are also likely identical.

FIG. 1 is a block diagram illustrating an embodiment of a relative finding system. In this example, relative finder system 102 may be implemented using one or more server computers having one or more processors, one or more special purpose computing appliances, or any other appropriate hardware, software, or combinations thereof. The operations of the relative finder system are described in greater detail below. In this example, various users of the system (e.g., user 1 ("Alice") and user 2 ("Bob")) access the relative finder system via a network 104 using client devices such as 106 and 108. User information (including genetic information and optionally other personal information such as family information, population group, etc.) pertaining to the users is stored in a database 110, which can be implemented on an integral storage component of the relative finder system, an attached storage device, a separate storage device accessible by the relative finder system, or a combination thereof. Many different arrangements of the physical components are possible in various embodiments. In various embodiments, the entire genome sequences or assayed DNA markers (SNPs, STRs, CNVs, etc.) are stored in the database to facilitate the relative finding process. For example, approximately 650,000 SNPs per individual's genome are assayed and stored in the database in some implementations.

System 100 shown in this example includes genetic and other additional non-genetic information for many users. By comparing the recombinable DNA information to identify IBD regions between various users, the relative finder system can identify users within the database that are relatives. Since more distant relationships (second cousins or further) are often unknown to the users themselves, the system allows the users to "opt-in" and receive notifications about the existence of relative relationships. Users are also presented with the option of connecting with their newly found relatives.

Figure 2:
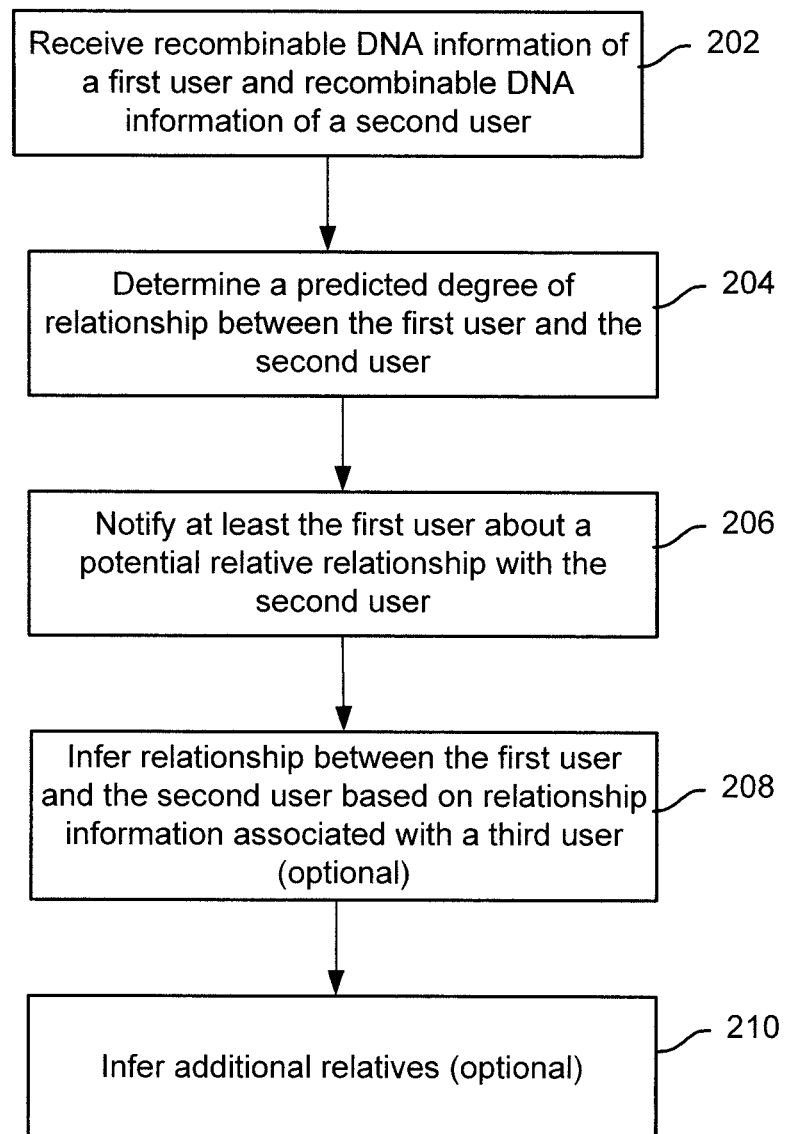
FIG. 2 is a flowchart illustrating an embodiment of a process for finding relatives in a relative finding system.

FIG. 2 is a flowchart illustrating an embodiment of a process for finding relatives in a relative finding system. Process 200 may be implemented on a relative finder system such as 100. The process may be invoked, for example, at a user's request to look for potential relatives this user may have in the database or by the system to assess the potential relationships among various users. At 202, recombinable DNA information of a first user (e.g., Alice) and of a second user (e.g., Bob) is received. In some embodiments, the information is retrieved from a database that stores recombinable DNA information of a plurality of users as well as any additional user information. For purposes of illustration, SNP information is described extensively in this and following examples. Other DNA information such as STR information and/or CNV information may be used in other embodiments.

At 204, a predicted degree of relationship between Alice and Bob is determined. In some embodiments, a range of possible relationships between the users is determined and a prediction of the most likely relationship between the users is made. In some embodiments, it is optionally determined whether the predicted degree of relationship at least meets a threshold. The threshold may be a user configurable value, a system default value, a value configured by the system's operator, or any other appropriate value. For example, Bob may select five generations as the maximum threshold, which means he is interested in discovering relatives with whom the user shares a common ancestor five generations or closer. Alternatively, the system may set a default value minimum of three generations, allowing the users to by default find relatives sharing a common ancestor at least three generations out or beyond. In some embodiments, the system, the user, or both, have the option to set a minimum threshold (e.g., two generations) and a maximum threshold (e.g., six generations) so that the user would discover relatives within a maximum number of generations, but would not be surprised by the discovery of a close relative such as a sibling who was previously unknown to the user.

At 206, Alice or Bob (or both) is notified about her/his relative relationship with the other user. In some embodiments, the system actively notifies the users by sending messages or alerts about the relationship information when it becomes available. Other notification techniques are possible, for example by displaying a list or table of users that are found to be related to the user. Depending on system settings, the potential relatives may be shown anonymously for privacy protection, or shown with visible identities to facilitate making connections. In embodiments where a threshold is set, the user is only notified if the predicted degree of relationship at least meets the threshold. In some embodiments, a user is only notified if both of the user and the potential relative have "opted in" to receive the notification. In various embodiments, the user is notified about certain personal information of the potential relative, the predicted relationship, the possible range of relationships, the amount of DNA matching, or any other appropriate information.

In some embodiments, at 208, the process optionally infers additional relationships or refines estimates of existing relationships between the users based on other relative relationship information, such as the relative relationship information the users have with a third user. For example, although Alice and Bob are only estimated to be $6^{th}$ cousins after step 204, if among Alice's relatives in the system, a third cousin, Cathy, is also a sibling of Bob's, then Alice and Bob are deemed to be third cousins because of their relative relationships to Cathy. The relative relationships with the third user may be determined based on genetic information and analysis using a process similar to 200, based on non-genetic information such as family tree supplied by one of the users, or both.

In some embodiments, the relatives of the users in the system are optionally checked to infer additional relatives at 210. For example, if Bob is identified as a third cousin of Alice's, then Bob's relatives in the system (such as children, siblings, possibly some of the parents, aunts, uncles, cousins, etc.) are also deemed to be relatives of Alice's. In some embodiments a threshold is applied to limit the relationships within a certain range. Additional notifications about these relatives are optionally generated.

Figure 3:
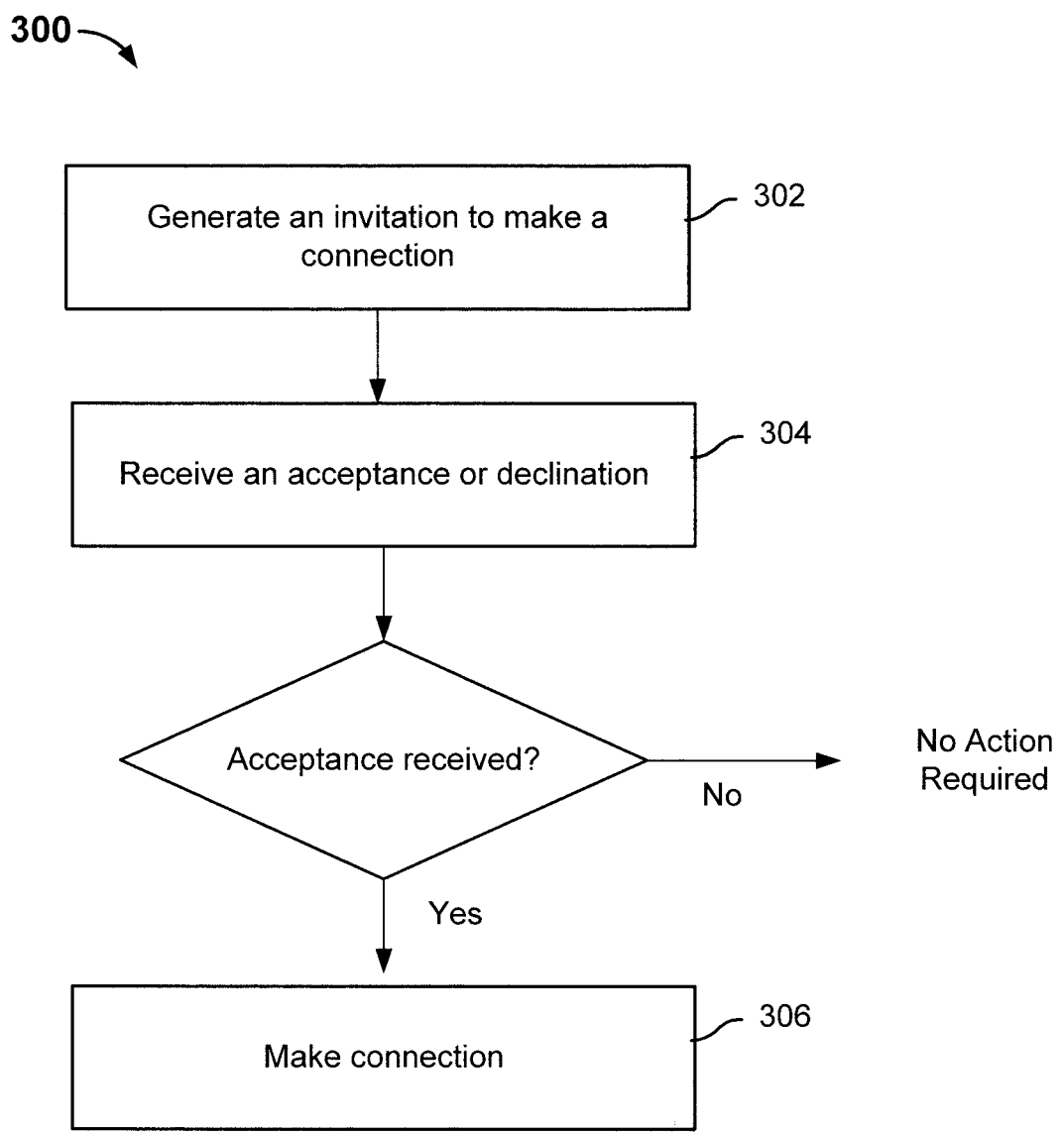
FIG. 3 is a flowchart illustrating an embodiment of a process for connecting a user with potential relatives found in the database.

Upon receiving a notification about another user who is a potential relative, the notified user is allowed to make certain choices about how to interact with the potential relative. FIG. 3 is a flowchart illustrating an embodiment of a process for connecting a user with potential relatives found in the database. The process may be implemented on a relative finder system such as 102, a client system such as 106, or a combination thereof. In this example, it is assumed that it has been determined that Alice and Bob are possibly 4th cousins and that Alice has indicated that she would like to be notified about any potential relatives within 6 generations. In this example, process 300 follows 206 of process 200, where a notification is sent to Alice, indicating that a potential relative has been identified. In some embodiments, the identity of Bob is disclosed to Alice. In some embodiments, the identity of Bob is not disclosed initially to protect Bob's privacy.

Upon receiving the notification, Alice decides that she would like to make a connection with the newly found relative. At 302, an invitation from Alice to Bob inviting Bob to make a connection is generated. In various embodiments, the invitation includes information about how Alice and Bob may be related and any personal information Alice wishes to share such as her own ancestry information. Upon receiving the invitation, Bob can accept the invitation or decline. At 304, an acceptance or a declination is received. If a declination is received, no further action is required. In some embodiments, Alice is notified that a declination has been received. If, however, an acceptance is received, at 306, a connection is made between Alice and Bob. In various embodiments, once a connection is made, the identities and any other sharable personal information (e.g., genetic information, family history, phenotype/traits, etc.) of Alice and Bob are revealed to each other and they may interact with each other. In some embodiments, the connection information is updated in the database.

In some embodiments, a user can discover many potential relatives in the database at once. Additional potential relatives are added as more users join the system and make their genetic information available for the relative finding process. FIGS. 4A-4I are screenshots illustrating user interface examples in connection with process 300. In this example, the relative finder application provides two views to the user: the discovery view and the list view.

Figure 4A:
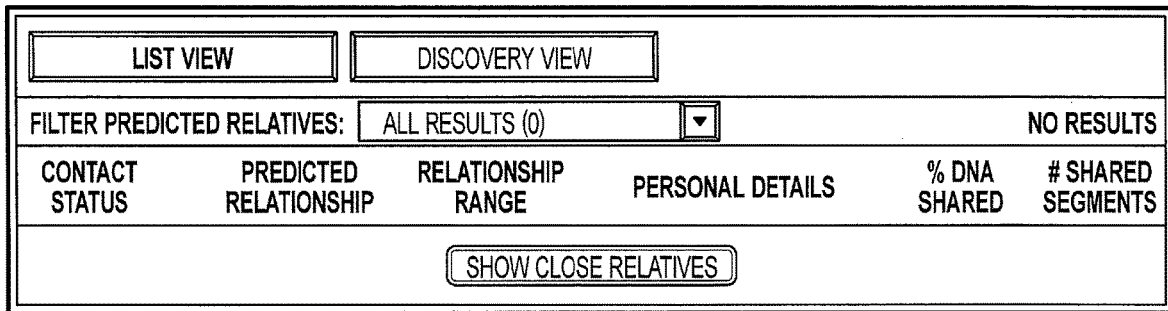
Figure 4B:
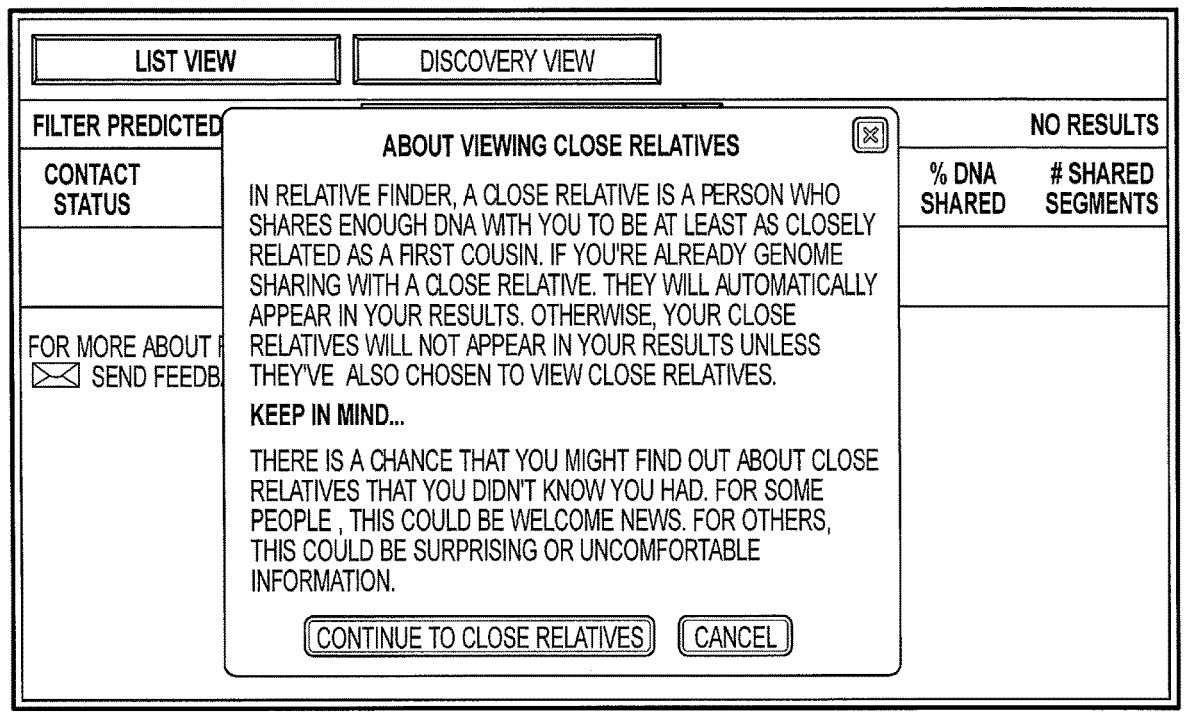

FIG. 4A shows an interface example for the discovery view at the beginning of the process. No relative has been discovered at this point. In this example, a privacy feature is built into the relative finder application so that close relative information will only be displayed if both the user and the close relative have chosen to view close relatives. This is referred to as the "opt in" feature. The user is further presented with a selection button "show close relatives" to indicate that he/she is interested in finding out about close relatives. FIG. 4B shows a message that is displayed when the user selects "show close relatives". The message explains to the user how a close relative is defined. In this case, a close relative is defined as a first cousin or closer. In other words, the system has set a default minimum threshold of three degrees. The message further explains that unless there is already an existing connection between the user and the close relative, any newly discovered potential close relatives will not appear in the results unless the potential close relatives have also chosen to view their close relatives. The message further warns about the possibility of finding out about close relatives the user did not know he/she had. The user has the option to proceed with viewing close relatives or cancel the selection.

FIG. 4C shows the results in the discovery view. In this example, seven potential relatives are found in the database. The predicted relationship, the range of possible relationship, certain personal details a potential relative has made public, the amount of DNA a potential relative shares with the user, and the number of DNA segments the potential relative shares with the user are displayed. The user is presented with a "make contact" selection button for each potential relative.

FIG. 4D shows the results in the list view. The potential relatives are sorted according to how close the corresponding predicted relationships are to the user in icon form. The user may select an icon that corresponds to a potential relative and view his/her personal information, the predicted relationship, relationship range, and other additional information. The user can also make contact with the potential relative.

Figure 4E:
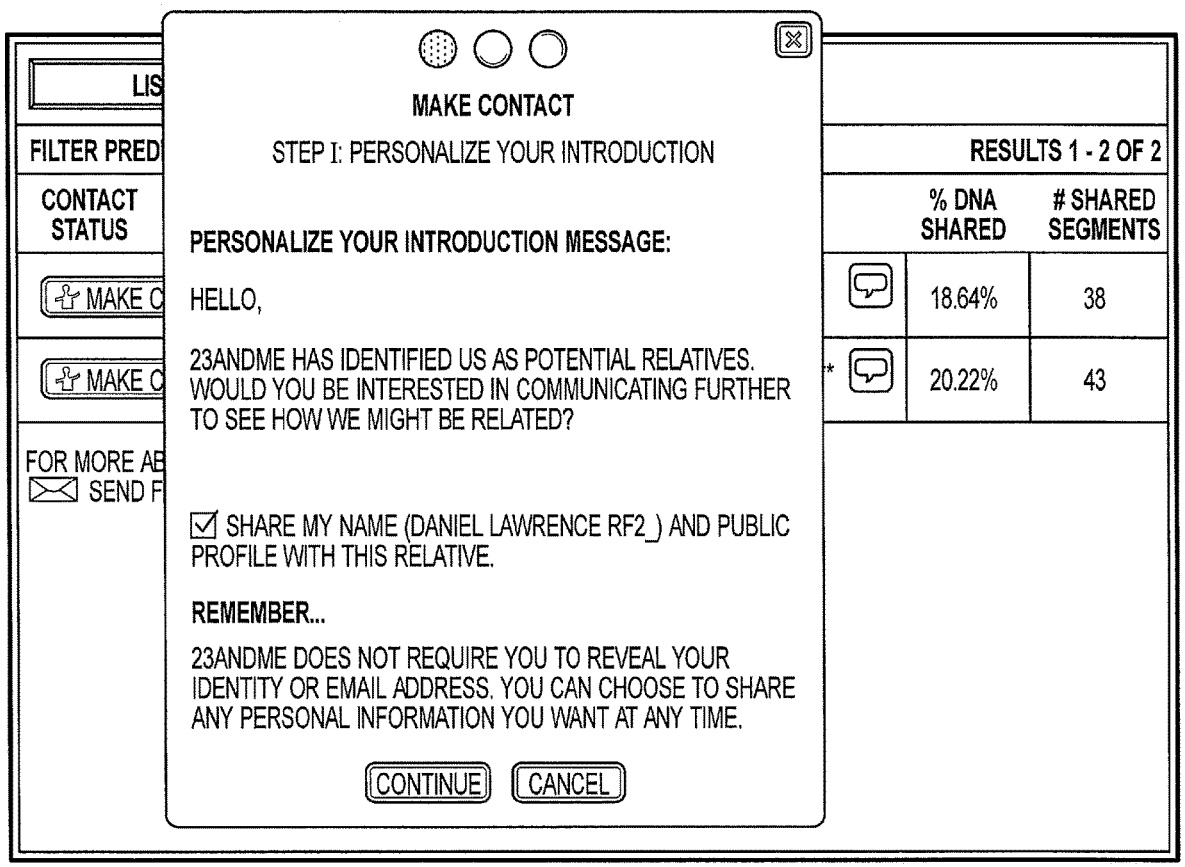
Figure 4F:
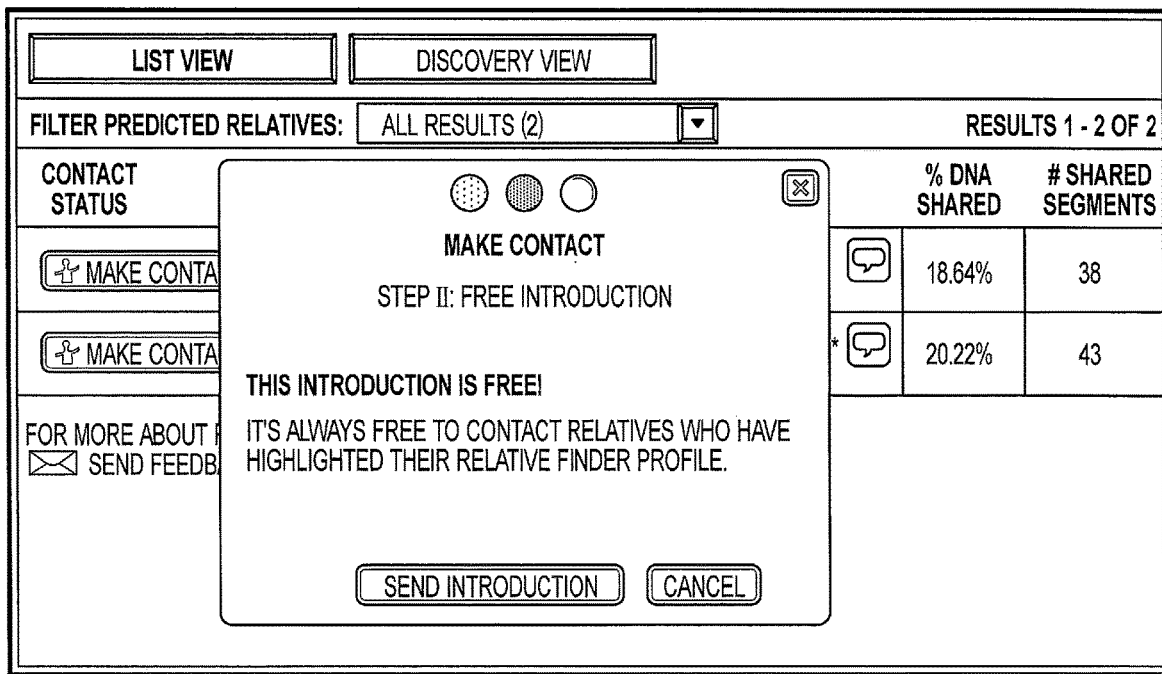
Figure 4G:
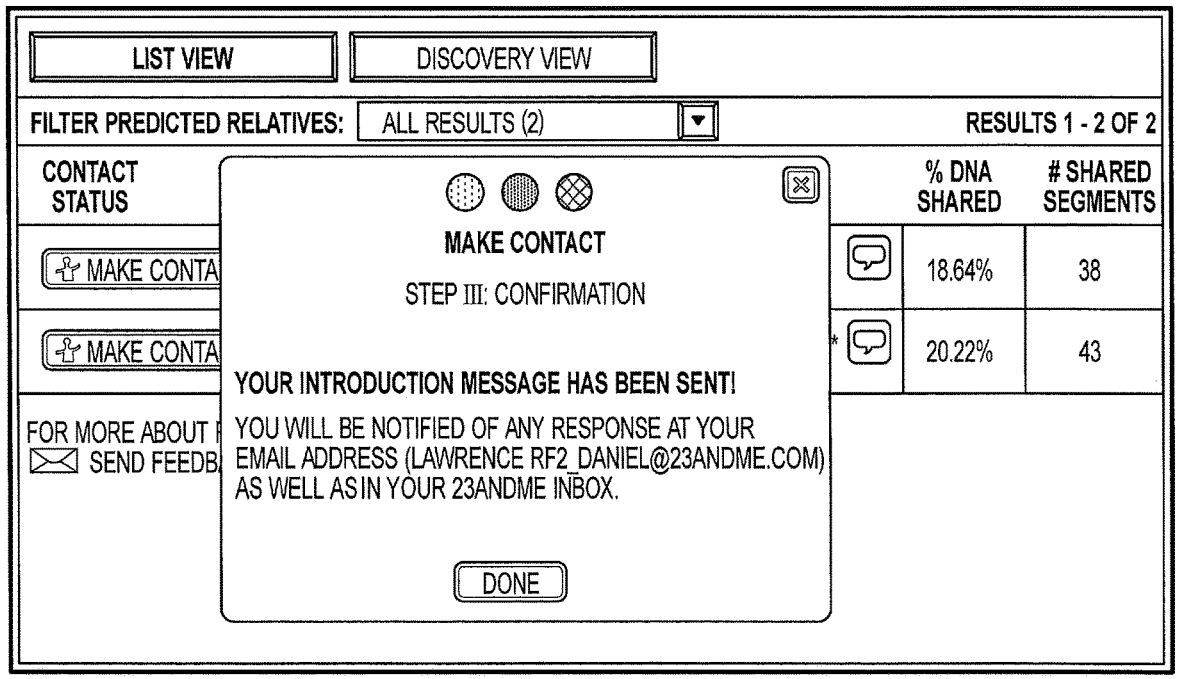

FIGS. 4E-4G show the user interface when the user selects to "make contact" with a potential relative. FIG. 4E shows the first step in making contact, where the user personalizes the introduction message and determine what information the user is willing to share with the potential relative. FIG. 4F shows an optional step in making contact, where the user is told about the cost of using the introduction service. In this case, the introduction is free. FIG. 4G shows the final step, where the introduction message is sent.

FIG. 4H shows the user interface shown to the potential relative upon receiving the introduction message. In this example, the discovery view indicates that a certain user/potential relative has requested to make a contact. The predicted relationship, personal details of the sender, and DNA sharing information are shown to the recipient. The recipient has the option to select "view message" to view the introduction message from the sender.

Figure 4I:
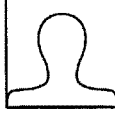

FIG. 4I shows the message as it is displayed to the recipient. In addition to the content of the message, the recipient is given the option to accept or decline the invitation to be in contact with the sender. If the recipient accepts the invitation, the recipient and the sender become connected and may view each other's information and/or interact with each other.

Many other user interfaces can be used in addition to or as alternatives of the ones shown above. For example, in some embodiments, at least some of the potential relatives are displayed in a family tree.

Determining the relationship between two users in the database is now described. In some embodiments, the determination includes comparing the DNA markers (e.g., SNPs) of two users and identifying IBD regions. The standard SNP based genotyping technology results in genotype calls each having two alleles, one from each half of a chromosome pair. As used herein, a genotype call refers to the identification of the pair of alleles at a particular locus on the chromosome. Genotype calls can be phased or unphased. In phased data, the individual's diploid genotype at a particular locus is resolved into two haplotypes, one for each chromosome. In unphased data, the two alleles are unresolved; in other words, it is uncertain which allele corresponds to which haplotype or chromosome.

The genotype call at a particular SNP location may be a heterozygous call with two different alleles or a homozygous call with two identical alleles. A heterozygous call is represented using two different letters such as AB that correspond to different alleles. Some SNPs are biallelic SNPs with only two possible states for SNPs. Some SNPs have more states, e.g. triallelic. Other representations are possible.

In this example, A is selected to represent an allele with base A and B represents an allele with base G at the SNP location. Other representations are possible. A homozygous call is represented using a pair of identical letters such as AA or BB. The two alleles in a homozygous call are interchangeable because the same allele came from each parent. When two individuals have opposite-homozygous calls at a given SNP location, or, in other words, one person has alleles AA and the other person has alleles BB, it is very likely that the region in which the SNP resides does not have IBD since different alleles came from different ancestors. If, however, the two individuals have compatible calls, that is, both have the same homozygotes (i.e., both people have AA alleles or both have BB alleles), both have heterozygotes (i.e., both people have AB alleles), or one has a heterozygote and the other a homozygote (i.e., one has AB and the other has AA or BB), there is some chance that at least one allele is passed down from the same ancestor and therefore the region in which the SNP resides is IBD. Further, based on statistical computations, if a region has a very low rate of opposite-homozygote occurrence over a substantial distance, it is likely that the individuals inherited the DNA sequence in the region from the same ancestor and the region is therefore deemed to be an IBD region.

Figure 5:
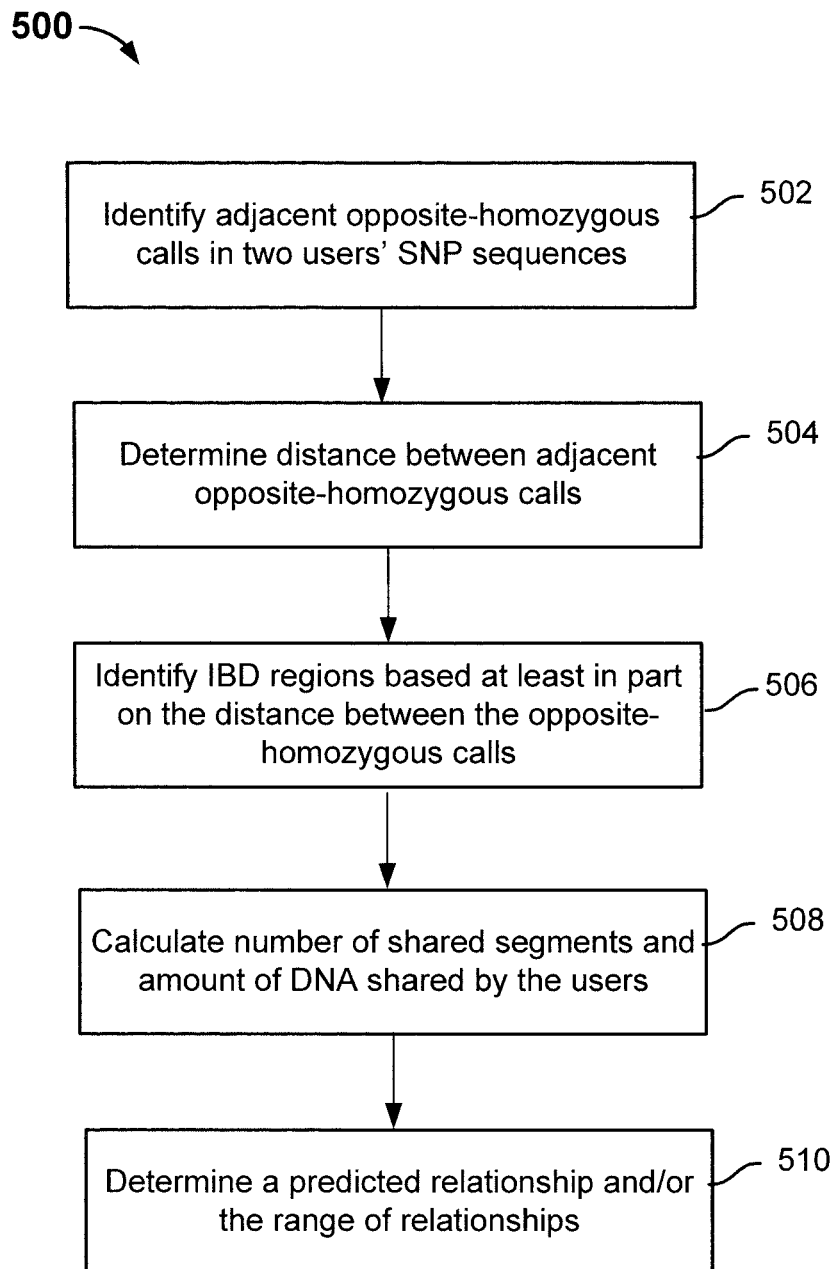
FIG. 5 is a diagram illustrating an embodiment of a process for determining the expected degree of relationship between two users.

FIG. 5 is a diagram illustrating an embodiment of a process for determining the predicted degree of relationship between two users. Process 500 may be implemented on a relative finder system such as 102 and is applicable to unphased data. At 502, consecutive opposite-homozygous calls in the users' SNPs are identified. The consecutive opposite-homozygous calls can be identified by serially comparing individual SNPs in the users' SNP sequences or in parallel using bitwise operations as described below. At 504, the distance between consecutive opposite-homozygous calls is determined. At 506, IBD regions are identified based at least in part on the distance between the opposite-homozygous calls. The distance may be physical distance measured in the number of base pairs or genetic distance accounting for the rate of recombination. For example, in some embodiments, if the genetic distance between the locations of two consecutive opposite-homozygous calls is greater than a threshold of 10 centimorgans (cM), the region between the calls is determined to be an IBD region. This step may be repeated for all the opposite-homozygous calls. A tolerance for genotyping error can be built by allowing some low rate of opposite homozygotes when calculating an IBD segment. In some embodiments, the total number of matching genotype calls is also taken into account when deciding whether the region is IBD. For example, a region may be examined where the distance between consecutive opposite homozygous calls is just below the 10 cM threshold. If a large enough number of genotype calls within that interval match exactly, the interval is deemed IBD.

Figure 6:
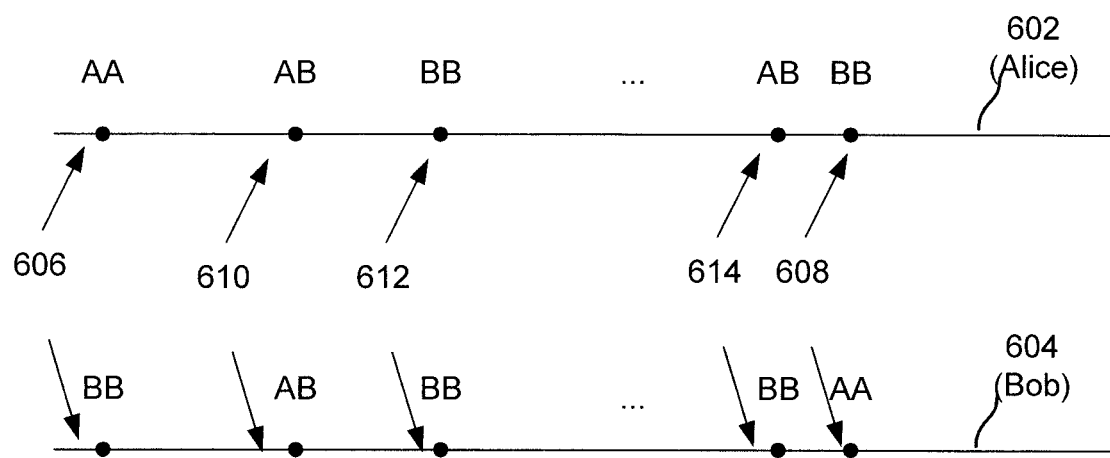
FIG. 6 is a diagram illustrating example DNA data used for IBD identification by process 500.

FIG. 6 is a diagram illustrating example DNA data used for IBD identification by process 500. 602 and 604 correspond to the SNP sequences of Alice and Bob, respectively. At location 606, the alleles of Alice and Bob are opposite-homozygotes, suggesting that the SNP at this location resides in a non-IBD region. Similarly, at location 608, the opposite-homozygotes suggest a non-IBD region. At location 610, however, both pairs of alleles are heterozygotes, suggesting that there is potential for IBD. Similarly, there is potential for IBD at location 612, where both pairs of alleles are identical homozygotes, and at location 614, where Alice's pair of alleles is heterozygous and Bob's is homozygous. If there is no other opposite-homozygote between 606 and 608 and there are a large number of compatible calls between the two locations, it is then likely that the region between 606 and 608 is an IBD region.

Returning to FIG. 5, at 508, the number of shared IBD segments and the amount of DNA shared by the two users are computed based on the IBD. In some embodiments, the longest IBD segment is also determined. In some embodiments, the amount of DNA shared includes the sum of the lengths of IBD regions and/or percentage of DNA shared. The sum is referred to as $IBD_{half}$ or half IBD because the individuals share DNA identical by descent for at least one of the homologous chromosomes. At 510, the predicted relationship between the users, the range of possible relationships, or both, is determined using the $IBD_{half}$ and number of segments, based on the distribution pattern of $IBD_{half}$ and shared segments for different types of relationships. For example, in a first degree parent/child relationship, the individuals have $IBD_{half}$ that is 100% the total length of all the autosomal chromosomes and 22 shared autosomal chromosome segments; in a second degree grandparent/grandchild relationship, the individuals have $IBD_{half}$ that is approximately half the total length of all the autosomal chromosomes and many more shared segments; in each subsequent degree of relationship, the percentage of $IBD_{half}$ of the total length is about 50% of the previous degree. Also, for more distant relationships, in each subsequent degree of relationship, the number of shared segments is approximately half of the previous number.

In various embodiments, the effects of genotyping error are accounted for and corrected. In some embodiments, certain genotyped SNPs are removed from consideration if there are a large number of Mendelian errors when comparing data from known parent/offspring trios. In some embodiments, SNPs that have a high no-call rate or otherwise failed quality control measures during the assay process are removed. In some embodiments, in an IBD segment, an occasional opposite-homozygote is allowed if there is sufficient opposite-homozygotes-free distance (e.g., at least 3 cM and 300 SNPs) surrounding the opposite-homozygote.

Figure 7:
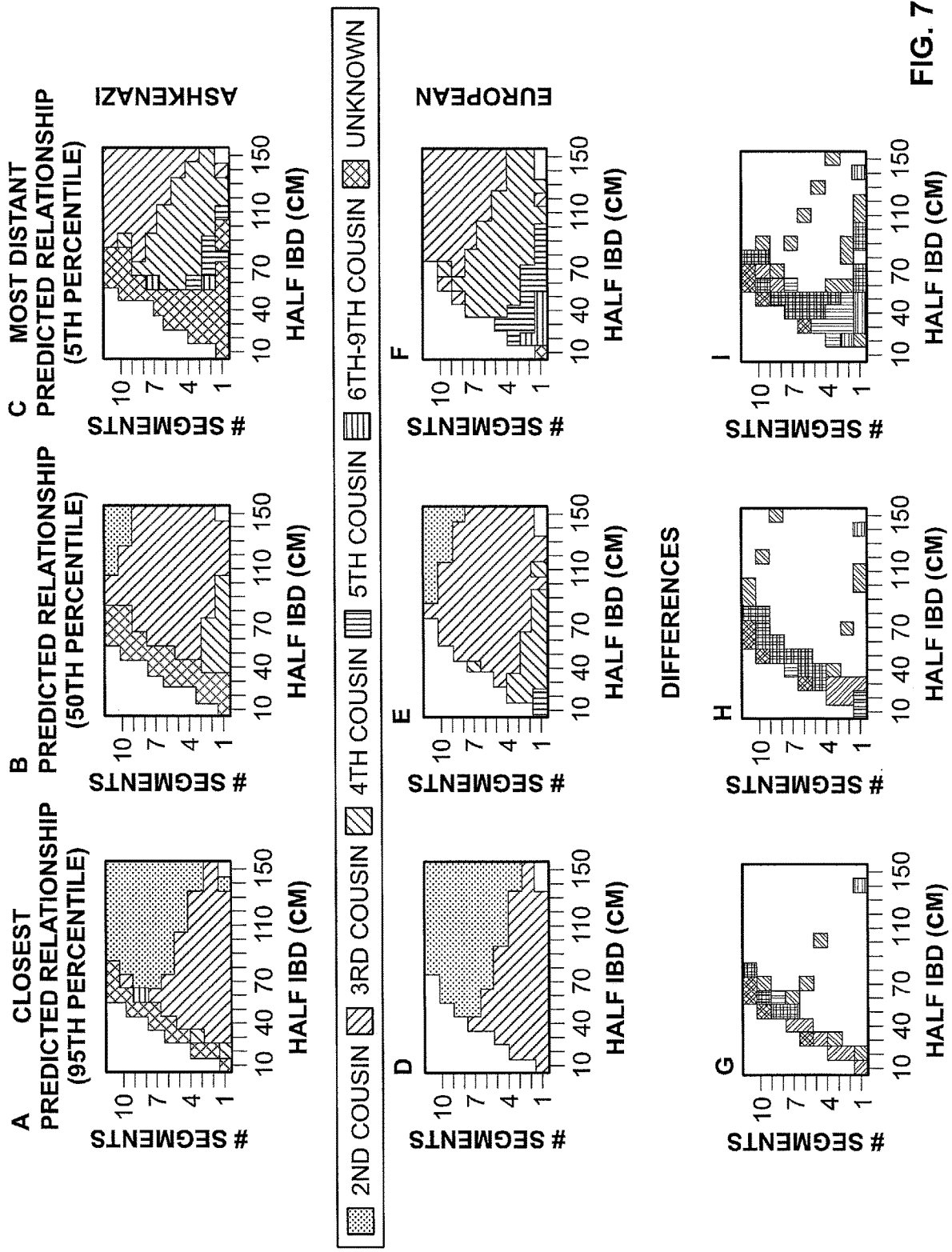
FIG. 7 shows the simulated relationship distribution patterns for different population groups according to one embodiment.

There is a statistical range of possible relationships for the same $IBD_{half}$ and shared segment number. In some embodiments, the distribution patterns are determined empirically based on survey of real populations. Different population groups may exhibit different distribution patterns. For example, the level of homozygosity within endogamous populations is found to be higher than in populations receiving gene flow from other groups. In some embodiments, the bounds of particular relationships are estimated using simulations of IBD using generated family trees. Based at least in part on the distribution patterns, the $IBD_{half}$ and shared number of segments, the degree of relationship between two individuals can be estimated. FIG. 7 shows the simulated relationship distribution patterns for different population groups according to one embodiment. In particular, Ashkenazi Jews and Europeans are two population groups surveyed. In panels A-C, for each combination of $IBD_{half}$ and the number of IBD segments in an Ashkenazi sample group, the 95%, 50% and 5% of obtained nth degree cousinships from 1 million simulated pedigrees are plotted. In panels D-F, for each combination of $IBD_{half}$ and the number of IBD segments in a European sample group, the 95%, 50% and 5% of obtained nth degree cousinships from 1 million simulated pedigrees are plotted. In panels G-I, the differences between Ashkenazi and European distant cousinship for the prior panels are represented. Each nth cousinship category is scaled by the expected number of nth degree cousins given a model of population growth. Simulations are conducted by specifying an extended pedigree and creating simulated genomes for the pedigree by simulating the mating of individuals drawn from a pool of empirical genomes. Pairs of individuals who appear to share $IBD_{half}$ that was not inherited through the specified simulated pedigree are marked as "unknown" in panels A-F. Thus, special distribution patterns can be used to find relatives of users who have indicated that they belong to certain distinctive population groups such as the Ashkenazi.

The amount of IBD sharing is used in some embodiments to identify different population groups. For example, for a given degree of relationship, since Ashkenazi tend to have much more IBD sharing than non-Ashkenazi Europeans, users may be classified as either Ashkenazi or non-Ashkenazi Europeans based on the number and pattern of IBD matches.

In some embodiments, instead of, or in addition to, determining the relationship based on the overall number of IBD segments and percent DNA shared, individual chromosomes are examined to determine the relationship. For example, X chromosome information is received in some embodiments in addition to the autosomal chromosomes. The X chromosomes of the users are also processed to identify IBD. Since one of the X chromosomes in a female user is passed on from her father without recombination, the female inherits one X chromosome from her maternal grandmother and another one from her mother. Thus, the X chromosome undergoes recombination at a slower rate compared to autosomal chromosomes and more distant relationships can be predicted using IBD found on the X chromosomes.

In some embodiments, analyses of mutations within IBD segments can be used to estimate ages of the IBD segments and refine estimates of relationships between users.

In some embodiments, the relationship determined is verified using non-DNA information. For example, the relationship may be checked against the users' family tree information, birth records, or other user information.

Figure 8:
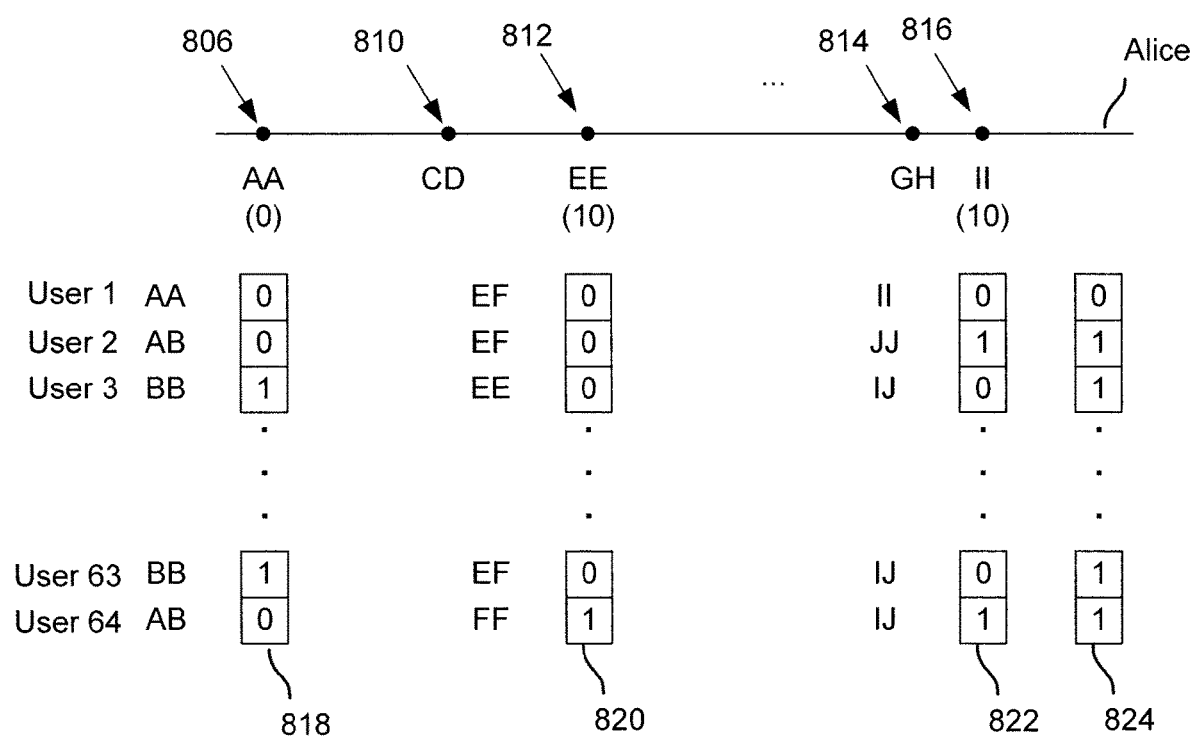
FIG. 8 is a diagram illustrating an embodiment of a highly parallel IBD identification process.

In some embodiments, the efficiency of IBD region identification is improved by comparing a user's DNA information with the DNA information of multiple other users in parallel and using bitwise operations. FIG. 8 is a diagram illustrating an embodiment of a highly parallel IBD identification process. Alice's SNP calls are compared with those of multiple other users. Alice's SNP calls are pre-processed to identify ones that are homozygous. Alice's heterozygous calls are not further processed since they always indicate that there is possibility of IBD with another user. For each SNP call in Alice's genome that is homozygous, the zygosity states in the corresponding SNP calls in the other users are encoded. In this example, compatible calls (e.g., heterozygous calls and same homozygous calls) are encoded as 0 and opposite-homozygous calls are encoded as 1. For example, for homozygous SNP call AA at location 806, opposite-homozygous calls BB are encoded as 1 and compatible calls (AA and AB) are encoded as 0; for homozygous SNP call EE at location 812, opposite-homozygous calls FF are encoded as 1 and compatible calls (EE and EF) are encoded as 0, etc. The encoded representations are stored in arrays such as 818, 820, and 824. In some embodiments, the length of the array is the same as the word length of the processor to achieve greater processing efficiency. For example, in a 64-bit processing system, the array length is set to 64 and the zygosity of 64 users' SNP calls are encoded and stored in the array.

A bitwise operation is performed on the encoded arrays to determine whether a section of DNA such as the section between locations 806 and 810 includes opposite-homozygous calls. In this example, a bitwise OR operation is performed to generate a result array 824. Any user with no opposite-homozygous calls between beginning location 806 and ending location 816 results in an entry value of 0 in array 824. The corresponding DNA segment, therefore, is deemed as an IBD region for such user and Alice. In contrast, users with opposite-homozygotes result in corresponding entry values of 1 in array 824 and they are deemed not to share IBD with Alice in this region. In the example shown, user 1 shares IBD with Alice while other users do not.

In some embodiments, phased data is used instead of unphased data. These data can come directly from assays that produce phased data, or from statistical processing of unphased data. IBD regions are determined by matching the SNP sequences between users. In some embodiments, sequences of SNPs are stored in dictionaries using a hashtable data structure for the ease of comparison. FIG. 9 is a diagram illustrating an example in which phased data is compared to identify IBD. The sequences are split along pre-defined intervals into non-overlapping words. Other embodiments may use overlapping words. Although a preset length of 3 is used for purposes of illustration in the example shown, many implementations may use words of longer lengths (e.g. 100). Also, the length does not have to be the same for every location. In FIG. 9, in Alice's chromosome pair 1, chromosome 902 is represented by words AGT, CTG, CAA, . . . and chromosome 904 is represented by CGA, CAG, TCA, . . . . At each location, the words are stored in a hash table that includes information about a plurality of users to enable constant retrieval of which users carry matching haplotypes. Similar hash tables are constructed for other sequences starting at other locations. To determine whether Bob's chromosome pair 1 shares any IBD with Alice's, Bob's sequences are processed into words at the same locations as Alice's. Thus, Bob's chromosome 906 yields CAT, GAC, CCG, . . . and chromosome 908 yields AAT, CTG, CAA, . . . . Every word from Bob's chromosomes is then looked up in the corresponding hash table to check whether any other users have the same word at that location in their genomes. In the example shown, the second and third words of chromosome 908 match second and third words of Alice's chromosome 902. This indicates that SNP sequence CTGCAA is present in both chromosomes and suggests the possibility of IBD sharing. If enough matching words are present in close proximity to each other, the region would be deemed IBD.

In some embodiments, relative relationships found using the techniques described above are used to infer characteristics about the users that are related to each other. In some embodiments, the inferred characteristic is based on non-genetic information pertaining to the related users. For example, if a user is found to have a number of relatives that belong to a particular population group, then an inference is made that the user may also belong to the same population group. In some embodiments, genetic information is used to infer characteristics, in particular characteristics specific to shared IBD segments of the related users. Assume, for example, that Alice has sequenced her entire genome but her relatives in the system have only genotyped SNP data. If Alice's genome sequence indicates that she may have inherited a disease gene, then, with Alice's permission, Alice's relatives who have shared IBD with Alice in the same region that includes the disease gene may be notified that they are at risk for the same disease.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A method of operating a relative finder database with hundreds of thousands of genetic markers to display a list of potential relatives among users in the relative finder database, comprising:

retrieving autosomal deoxyribonucleic acid (DNA) sequence information of a first user and a plurality of users in the relative finder database, wherein the autosomal DNA sequence information comprises hundreds of thousands of genetic markers;

receiving an opt-in election from the first user provided through a user interface to consent to be presented with a list of potential relatives among users in the relative finder database;

processing in parallel, responsive to the opt-in election and using one or more computer processors, the hundreds of thousands of genetic markers of the first user and the plurality of users to estimate one or more identical-by-descent (IBD) segments between the first user and the plurality of users, wherein the processing in parallel comprises processing data of two or more users or two or more genetic markers in parallel;

estimating, using one or more computer processors, a number of such shared IBD segments and a length of such shared IBD segments between the first user and the plurality of users based on the one or more IBD segments;

applying, using one or more computer processors, a relationship estimate model to the number of such shared IBD segments and the length of such shared IBD segments between the first user and the plurality of users to estimate a degree of relative relationship between the first user and one or more users among the plurality of users of the database who share a common ancestor within a threshold number of generations, wherein the one or more users among the plurality of users in the database were previously unknown to the first user; and presenting, responsive to a request from the first user received through a user interface, to the first user an interactive graphical user interface (GUI), wherein the interactive GUI comprises a graphical display structure displaying the first user, the one or more users who may be potential relatives, and information pertaining to each of the one or more users including the estimated degree of relative relationship between the first user and each of the one or more users.

2. The method of claim 1, wherein the processing in parallel comprises looking up a genetic marker of the first user in one or more hash tables constructed using the genetic marker of the plurality of users, thereby estimating that the genetic marker of the first user matches the genetic marker of a second user, the second user being a user in the plurality of users.

3. The method of claim 2, further comprising: estimating an IBD segment including the genetic marker shared between the first user and the second user.

4. The method of claim 2, wherein said genetic marker is encoded as a part of a word comprising a plurality of genetic markers.

5. The method of claim 1, wherein the processing in parallel comprises:

making consecutive opposite homozygous calls by comparing the two or more genetic markers between the first user and the plurality of users and determining whether each genetic marker comprises an opposite homozygous call between the first user and each user of the plurality of users; and encoding the opposite homozygous call data in an array comprising two or more rows corresponding to the two or more users and two or more columns corresponding to the two or more genetic markers.

6. The method of claim 5, further comprising: performing a bitwise operation on the array to estimate an IBD segment.

7. The method of claim 5, wherein the two or more users comprise at least 64 users.

8. The method of claim 1, wherein the relationship estimate model comprises relationship distributions for combinations of various numbers of such shared IBD segments and various lengths of such shared IBD segments, the relationship distributions being obtained from a plurality of pedigrees.

9. The method of claim 3, wherein application of the relationship estimate model provides an estimated relative relationship based on a $50^{th}$ percentile relationship pattern, and an estimated range of relative relationship based on a $95^{th}$ percentile relationship pattern and a $5^{th}$ percentile relationship pattern.

10. The method of claim 8, wherein the plurality of pedigrees comprises computer simulated individuals whose genomes are obtained by mating, by computer simulation, genomes of actual individuals.

11. The method of claim 1, wherein the genetic markers comprise 650,000 genetic markers.

12. The method of claim 1, wherein the genetic markers comprise 650,000 Single Nucleotide Polymorphisms (SNPs).

13. The method of claim 1, wherein the genetic markers comprise Single Nucleotide Polymorphisms (SNPs).

14. The method of claim 1, wherein the information pertaining to each of the one or more users comprises:

an entry of personal details that each of the one or more users has chosen to make public;

the number of the IBD segments shared between the first user and each of the one or more users;

the length of the IBD segments shared between the first user and each of the one or more users or the length represented as a percentage; and the estimated degree of relative relationship between the first user and each of the one or more users.

15. The method of claim 14, further comprising: estimating with the relationship estimate model a range of possible relative relationships between the first user and each of the one or more users among the plurality of users in the database; and the graphical display structure further comprising: the range of possible relative relationships between the first user and each of the one or more users among the plurality of users in the database.

16. The method of claim 1, wherein the graphical display structure comprises a list of the one or more users sorted in descending order with a closest estimated relative positioned at the top of the list.

17. The method of claim 16, the graphical display structure further comprising: a family tree representation of the multiple users based on the estimated degree of relative relationship between the first user and each of the multiple users.

18. The method of claim 1, the relationship estimate model further comprising: a feature corresponding to genetic ethnicity or self-reported ethnicity.

19. The method of claim 1, wherein the autosomal DNA sequence information includes genotype data, the relationship estimate model further comprising: a feature accounting for genotyping errors.

20. The method of claim 1, wherein each IBD segment exceeds a predetermined genetic distance threshold.

21. The method of claim 18, wherein the predetermined genetic distance threshold is 10 centimorgans (10 cM).

22. The method of claim 1, wherein one or more computer processors are configured to estimate the one or more IBD segments by assessing a genetic distance between consecutive opposite homozygous calls made regarding the first user and the plurality of users in the database.

23. The method of claim 22, wherein the genetic distance between the consecutive opposite homozygous calls is estimating by:

estimating a physical distance between the consecutive opposite homozygous calls;

manipulating the physical distance between consecutive opposite homozygous calls to account for recombination; and estimating the genetic distance between opposite homozygous calls based on the manipulated physical distances between the opposite homozygous calls.

24. The method of claim 22, further comprising: encoding the opposite homozygous calls between the first user and the plurality of users in the database in an array comprising a plurality of rows corresponding to the plurality of users in the database and a plurality of columns corresponding to a plurality of calls.

25. The method of claim 1, wherein the autosomal DNA sequence information includes entire genome sequence data.

26. The method of claim 1, wherein the length of such shared IBD segments includes a total length of the such shared IBD segments.

27. A computer system comprising one or more processors and system memory, the one or more processors being configured to:
retrieve autosomal deoxyribonucleic acid (DNA) sequence information of a first user and a plurality of users in a relative finder database, wherein the autosomal DNA sequence information comprises hundreds of thousands of genetic markers;
receive an opt-in election from the first user provided through a user interface to consent to be presented with a list of potential relatives among users in the relative finder database;
process in parallel, responsive to the opt-in election and using one or more computer processors, the hundreds of thousands of genetic markers of the first user and the plurality of users to estimate one or more identical-by-descent (IBD) segments between the first user and the plurality of users, wherein the processing in parallel comprises processing data of two or more users or two or more genetic markers in parallel;
estimate a number of such shared IBD segments and a length of such shared IBD segments between the first user and the plurality of users based on the one or more such shared IBD segments, wherein the length of the such shared IBD segments is estimated as a genetic distance;
apply a relationship estimate model to the number of such shared IBD segments and the length of such shared IBD segments between the first user and the plurality of users to estimate a degree of relative relationship between the first user and one or more users among the plurality of users of the relative finder database who share a common ancestor within a threshold number of generations, wherein the one or more users among the plurality of users in the relative finder database were previously unknown to the first user; and
present, responsive to a request from the first user received through a user interface, to the first user an interactive graphical user interface (GUI), wherein the interactive GUI comprises a graphical display structure displaying the first user, the one or more users who may be potential relatives, and information pertaining to each of the one or more users including the estimated degree of relative relationship between the first user and each of the one or more users.

28. The system of claim 27, wherein the information pertaining to each of the one or more users comprises:
an entry of personal details that each of the one or more users has chosen to make public;
the number of such shared IBD segments shared between the first user and each of the one or more users;
the length of the IBD segments shared between the first user and each of the one or more users or the length represented as a percentage; and
the estimated degree of relative relationship between the first user and each of the one or more users.

29. A computer program product comprising a non-transitory computer readable medium having stored thereon program code that, when executed by one or more processors of a computer system, cause the computer system to perform operations for operating a relative finder database with hundreds of thousands of genetic markers to display a list of potential relatives among users in the relative finder database, said program code comprising code for:
retrieving autosomal deoxyribonucleic acid (DNA) sequence information of a first user and a plurality of users in the relative finder database, wherein the autosomal DNA sequence information comprises hundreds of thousands of genetic markers;
receiving an opt-in election from the first user provided through a user interface to consent to be presented with a list of potential relatives among users in the relative finder database;
processing in parallel, responsive to the opt-in election and using one or more computer processors, the hundreds of thousands of genetic markers of the first user and the plurality of users to estimate one or more identical-by-descent (IBD) segments between the first user and the plurality of users, wherein the processing in parallel comprises processing data of two or more users or two or more genetic markers in parallel;
estimating a number of such shared IBD segments and a length of such shared IBD segments between the first user and the plurality of users based on the one or more IBD segments;
applying a relationship estimate model to the number of such shared IBD segments and the length of such shared IBD segments between the first user and the plurality of users to estimate a degree of relative relationship between the first user and one or more users among the plurality of users of the database who share a common ancestor within a threshold number of generations, wherein the one or more users among the plurality of users in the database were previously unknown to the first user; and
presenting, responsive to a request from the first user received through a user interface, to the first user an interactive graphical user interface (GUI), wherein the interactive GUI comprises a graphical display structure displaying the first user, the one or more users who may be potential relatives, and information pertaining to each of the one or more users including the estimated degree of relative relationship between the first user and each of the one or more users.

30. A method of operating a relative finder database with hundreds of thousands of genetic markers to display a list of potential relatives among users in the relative finder database, comprising:
retrieving autosomal deoxyribonucleic acid (DNA) sequence information of a first user and a plurality of users in the relative finder database, wherein the autosomal DNA sequence information comprises hundreds of thousands of genetic markers;
receiving an opt-in election from the first user provided through a user interface to consent to be presented with a list of potential relatives among users in the relative finder database;

processing in parallel, responsive to the opt-in election and using one or more computer processors, the hundreds of thousands of genetic markers of the first user and the plurality of users to estimate one or more identical-by-descent (IBD) segments between the first user and the plurality of users, wherein the processing in parallel comprises processing data of two or more users or two or more genetic markers in parallel, wherein the processing in parallel comprises:
  making consecutive opposite homozygous calls by comparing the two or more genetic markers between the first user and the plurality of users and determining whether each genetic marker comprises an opposite homozygous call between the first user and each user of the plurality of users, and
  encoding the opposite homozygous call data in an array comprising two or more rows corresponding to the two or more users and two or more columns corresponding to the two or more genetic markers;
estimating, using one or more computer processors, a number of such shared IBD segments and a length of such shared IBD segments between the first user and the plurality of users based on the one or more IBD segments;
applying, using one or more computer processors, a relationship estimate model to the number of such shared IBD segments and the length of such shared IBD segments between the first user and the plurality of users to estimate a degree of relative relationship between the first user and one or more users among the plurality of users of the database who share a common ancestor within a threshold number of generations, wherein the one or more users among the plurality of users in the database were previously unknown to the first user; and
presenting, responsive to a request from the first user received through a user interface, to the first user an interactive graphical user interface (GUI), wherein the interactive GUI comprises a graphical display structure displaying the first user, the one or more users who may be potential relatives, and information pertaining to each of the one or more users including the estimated degree of relative relationship between the first user and each of the one or more users.

* * * * *